(12) United States Patent
Donaldson et al.

(10) Patent No.: US 12,324,894 B2
(45) Date of Patent: *Jun. 10, 2025

(54) PERCUTANEOUS ACCESS PATHWAY SYSTEM

(71) Applicant: Critical Innovations, LLC, Lawndale, CA (US)

(72) Inventors: Ross I. Donaldson, Lawndale, CA (US); Oliver Buchanan, Lawndale, CA (US); Tim Fisher, Lawndale, CA (US); Jon Armstrong, Lawndale, CA (US); John Cambridge, Lawndale, CA (US)

(73) Assignee: Critical Innovations LLC, Lawndale, CA (US)

( * ) Notice: Subject to any disclaimer, the term of this patent is extended or adjusted under 35 U.S.C. 154(b) by 383 days.

This patent is subject to a terminal disclaimer.

(21) Appl. No.: 17/881,298

(22) Filed: Aug. 4, 2022

(65) Prior Publication Data

US 2022/0370780 A1     Nov. 24, 2022

Related U.S. Application Data

(63) Continuation of application No. 16/948,640, filed on Sep. 25, 2020, now Pat. No. 11,406,809, which is a
(Continued)

(51) Int. Cl.
*A61B 17/34*     (2006.01)
*A61B 17/00*     (2006.01)
(Continued)

(52) U.S. Cl.
CPC ......... *A61M 39/0247* (2013.01); *A61B 17/34* (2013.01); *A61B 17/3415* (2013.01);
(Continued)

(58) Field of Classification Search
CPC ...... A61M 39/0247; A61M 2039/0273; A61M 2039/0279; A61B 17/34; A61B 17/3415;
(Continued)

(56) References Cited

U.S. PATENT DOCUMENTS 3,777,757 A     12/1973     Gray et al.
3,789,853 A     2/1974     Kim et al.
(Continued)

FOREIGN PATENT DOCUMENTS

CN     1756513 B     4/2006
EP     2168558 A1     3/2010
(Continued)

OTHER PUBLICATIONS

EP Application No. 13179479.4, Search Report dated Nov. 8, 2013, 5 pages.
(Continued)

*Primary Examiner* — Ellen C Hammond
(74) *Attorney, Agent, or Firm* — Merchant & Gould P.C.

(57) ABSTRACT

An improved method and device are provided for forming and/or maintaining a percutaneous access pathway. The device generally comprises an access pathway and attachment device. The provided assembly substantially reduces the possibility of iatrogenic infection while accessing and/or re-accessing a body space.

13 Claims, 20 Drawing Sheets

Related U.S. Application Data continuation of application No. 16/113,707, filed on Aug. 27, 2018, now Pat. No. 10,814,119.

(60) Provisional application No. 62/562,183, filed on Sep. 22, 2017.

(51) Int. Cl.
  *A61B 90/40* (2016.01)
  *A61M 1/02* (2006.01)
  *A61M 39/02* (2006.01)
  *A61M 27/00* (2006.01)

(52) U.S. Cl.
  CPC ...... *A61B 17/3423* (2013.01); *A61B 17/3498* (2013.01); *A61B 90/40* (2016.02); *A61B 2017/00809* (2013.01); *A61B 2017/345* (2013.01); *A61B 2017/3492* (2013.01); *A61M 1/02* (2013.01); *A61M 27/00* (2013.01); *A61M 2039/0252* (2013.01); *A61M 2039/0258* (2013.01); *A61M 2039/0261* (2013.01); *A61M 2039/027* (2013.01); *A61M 2039/0276* (2013.01); *A61M 2039/0279* (2013.01); *A61M 2039/0288* (2013.01); *A61M 2210/101* (2013.01)

(58) Field of Classification Search
  CPC .......... A61B 17/3423; A61B 2017/345; A61B 2017/3492
  See application file for complete search history.

(56) References Cited

U.S. PATENT DOCUMENTS

| | | |
|---|---|---|
| 3,886,948 A | 6/1975 | Hakim |
| 3,894,540 A | 7/1975 | Bonner, Jr. |
| 4,153,058 A | 5/1979 | Nehme |
| 4,164,938 A | 8/1979 | Patton |
| 4,221,215 A | 9/1980 | Mandelbaum |
| 4,392,853 A | 7/1983 | Muto |
| 4,617,011 A | 10/1986 | Bloxom, Jr. |
| 4,664,660 A | 5/1987 | Goldberg et al. |
| 4,767,409 A | 8/1988 | Brooks |
| 4,767,411 A | 8/1988 | Edmunds |
| 4,809,694 A | 3/1989 | Ferrara |
| 4,944,724 A | 7/1990 | Goldeberg et al. |
| 5,098,388 A | 3/1992 | Kulkashi et al. |
| 5,207,647 A | 5/1993 | Phelps |
| 5,215,522 A | 6/1993 | Page et al. |
| 5,215,531 A | 6/1993 | Maxson et al. |
| 5,223,228 A | 6/1993 | Telang |
| 5,242,398 A | 9/1993 | Knoll |
| 5,256,148 A | 10/1993 | Smith et al. |
| 5,263,939 A | 11/1993 | Wortrich |
| 5,284,474 A | 2/1994 | Adair |
| 5,300,046 A | 4/1994 | Scarfone et al. |
| 5,334,159 A | 8/1994 | Turkel |
| 5,336,193 A | 9/1994 | Rom et al. |
| 5,376,082 A | 12/1994 | Phelps |
| 5,421,821 A | 6/1995 | Janicki |
| 5,429,608 A | 7/1995 | Rom et al. |
| 5,431,676 A | 7/1995 | Dubrul et al. |
| 5,478,333 A | 12/1995 | Asherman, Jr. |
| 5,489,290 A | 2/1996 | Furnish |
| 5,490,843 A | 2/1996 | Hildwein et al. |
| 5,514,111 A | 5/1996 | Phelps |
| 5,520,650 A | 5/1996 | Zadini et al. |
| 5,545,179 A | 8/1996 | Williamson, IV |
| 5,562,677 A | 10/1996 | Hildwein et al. |
| 5,658,271 A | 8/1997 | Loubser |
| 5,660,883 A | 8/1997 | Omura |
| 5,662,616 A | 9/1997 | Bousquet |
| 5,685,852 A | 11/1997 | Turkel et al. |
| 5,707,362 A | 1/1998 | Yoon |
| 5,776,110 A | 7/1998 | Guy et al. |
| 5,807,341 A | 9/1998 | Heim |
| 5,725,506 A | 10/1998 | Freeman et al. |
| 5,827,221 A | 10/1998 | Phelps |
| 5,830,191 A | 11/1998 | Hildwein et al. |
| 5,897,531 A | 4/1999 | Amirana |
| 5,902,273 A | 5/1999 | Yang et al. |
| 5,997,486 A | 12/1999 | Burek et al. |
| 6,018,094 A | 1/2000 | Fox |
| 6,019,735 A | 2/2000 | Kensey et al. |
| 6,162,236 A | 12/2000 | Osada |
| 6,221,048 B1 | 4/2001 | Phelps |
| 6,325,812 B1 | 12/2001 | Dubrul et al. |
| 6,402,770 B1 | 6/2002 | Jessen |
| 6,447,483 B1 | 9/2002 | Steube et al. |
| 6,447,489 B1 | 9/2002 | Peterson |
| 6,517,519 B1 | 2/2003 | Rosen et al. |
| 6,605,063 B2 | 8/2003 | Bousquet |
| 6,638,253 B2 | 10/2003 | Breznock |
| 6,770,070 B1 | 8/2004 | Balbierz |
| 6,905,484 B2 | 6/2005 | Buckman et al. |
| 7,135,010 B2 | 11/2006 | Buckman et al. |
| 7,229,433 B2 | 6/2007 | Mullen |
| 7,244,245 B2 | 7/2007 | Purow et al. |
| 7,429,687 B2 | 9/2008 | Kauth et al. |
| 7,533,696 B2 | 5/2009 | Paul, Jr. |
| 7,615,674 B2 | 11/2009 | Asherman |
| 7,771,437 B2 | 8/2010 | Hogg |
| 7,776,003 B2 | 8/2010 | Zauner |
| 7,789,873 B2 | 9/2010 | Kubalak et al. |
| 7,811,293 B2 | 10/2010 | Simpson et al. |
| 7,824,366 B2 | 11/2010 | Tanaka |
| 7,842,058 B2 | 11/2010 | Simpson |
| 7,892,170 B2 | 2/2011 | Moreno et al. |
| 7,896,897 B2 | 3/2011 | Gresham et al. |
| 8,057,443 B2 | 11/2011 | McNeil |
| 8,062,315 B2 | 11/2011 | Aster et al. |
| 8,128,648 B2 | 3/2012 | Hassidov et al. |
| 8,206,294 B2 | 6/2012 | Widenhouse |
| 8,257,251 B2 | 9/2012 | Shelton, IV et al. |
| 8,403,913 B2 | 3/2013 | Dein |
| 8,430,094 B2 | 4/2013 | Tanaka et al. |
| 8,518,053 B2 | 8/2013 | Tanaka et al. |
| 8,795,326 B2 | 8/2014 | Richard |
| 9,616,203 B2 | 4/2017 | Donaldson |
| 10,046,147 B2 | 8/2018 | Donaldson |
| 10,314,952 B2 | 6/2019 | Donaldson |
| 10,864,356 B2 | 12/2020 | Donaldson |
| 2003/0073960 A1 | 4/2003 | Adams et al. |
| 2003/0216770 A1 | 11/2003 | Persidsky et al. |
| 2003/0233073 A1 | 12/2003 | Purow et al. |
| 2004/0049222 A1 | 3/2004 | Schaeffer et al. |
| 2004/0073154 A1 | 4/2004 | Borgensen |
| 2004/0078026 A1 | 4/2004 | Wagner |
| 2004/0133226 A1 | 7/2004 | Buckman et al. |
| 2004/0199121 A1 | 10/2004 | Wenchell et al. |
| 2005/0203565 A1 | 9/2005 | Rethy et al. |
| 2006/0025723 A1 | 2/2006 | Ballarini |
| 2006/0041270 A1 | 2/2006 | Lenker et al. |
| 2006/0212062 A1 | 9/2006 | Farascioni |
| 2007/0021768 A1 | 1/2007 | Nance et al. |
| 2007/0038180 A1 | 2/2007 | Sinha et al. |
| 2008/0103451 A1 | 5/2008 | Schaefer, Jr. et al. |
| 2008/0125750 A1 | 5/2008 | Gaissert |
| 2008/0312638 A1 | 12/2008 | McNeil |
| 2009/0005800 A1 | 1/2009 | Franer et al. |
| 2009/0030375 A1 | 1/2009 | Franer et al. |
| 2009/0205646 A1 | 8/2009 | Tanaka et al. |
| 2009/0205651 A1 | 8/2009 | Tanaka et al. |
| 2009/0209913 A1 | 8/2009 | Ferrari |
| 2009/0227987 A1 | 9/2009 | Singer |
| 2009/0318898 A1 | 12/2009 | Dein |
| 2009/0326465 A1 | 12/2009 | Richard |
| 2010/0170507 A1 | 7/2010 | Tanaka et al. |
| 2010/0204707 A1 | 8/2010 | Tanaka et al. |
| 2010/0249694 A1 | 9/2010 | Choi et al. |
| 2011/0054340 A1 | 3/2011 | Russ et al. |
| 2011/0152874 A1 | 6/2011 | Lyons |
| 2011/0201883 A1 | 8/2011 | Cooper et al. |

(56) References Cited

U.S. PATENT DOCUMENTS

| | | |
|---|---|---|
| 2012/0051967 A1 | 3/2012 | Murphy et al. |
| 2012/0191044 A1 | 7/2012 | Koike |
| 2012/0209166 A1 | 8/2012 | Power et al. |
| 2013/0131645 A1 | 5/2013 | Tekulve |
| 2014/0046303 A1 | 2/2014 | Donaldson |
| 2014/0257168 A1 | 9/2014 | Gill |
| 2014/0276416 A1 | 9/2014 | Nelson et al. |
| 2014/0276418 A1 | 9/2014 | Nelson et al. |
| 2014/0364821 A1 | 12/2014 | Gibbons |
| 2015/0182733 A1 | 7/2015 | Donaldson |
| 2016/0008081 A1 | 1/2016 | Forsell |
| 2016/0287111 A1 | 10/2016 | Jacobsen |
| 2017/0182229 A1 | 6/2017 | Donaldson |
| 2018/0296808 A1 | 10/2018 | Donaldson |
| 2019/0091459 A1 | 3/2019 | Donaldson et al. |
| 2019/0255228 A1 | 8/2019 | Donaldson |
| 2019/0358438 A1 | 11/2019 | Fortune et al. |
| 2021/0093843 A1 | 4/2021 | Donaldson |

FOREIGN PATENT DOCUMENTS

| | | |
|---|---|---|
| GB | 2140301 A | 11/1984 |
| WO | 20080291009 A1 | 3/2008 |

OTHER PUBLICATIONS

EP Application No. 14200292.2, Search Report dated May 22, 2015, 8 pages.

EP Application No. 13179479.4, Examination Report dated Feb. 7, 2017, 3 pages.

EP Application No. 13179479.4 Examination Report dated Oct. 5, 2017, 3 pages.

EP Application No. 14200292.2, Communication Pursuant to Article 94(3) dated Feb. 26, 2018, 6 pages.

EP Application No. 18195962.8, Extended EP Search Report dated Jan. 22, 2019.

Mabry et al., "Prehospital Advances in the Management of Severe Penetrating Trauma," Crit Care Med 2008, vol. 36, No. 7 (Suppl.), 9 pages.

Leigh-Smith et al., "Tension Pneumothorax-time for Re-think?," Emerg Med J 2005, vol. 22, pp. 8-16.

Maxwell et al., "The Hanging Drop to Locate the Pleural Space: A Safer Method for Decompression of Suspected Tension Pneumothorax?," The Journal of Trauma, Injury, Infection, and Critical Care, vol. 69, No., 4, Oct. 2010, 2 pages.

Bassett et al., "Design of a Mechanical Clutch-Based Needle-Insertion Device," PNAS Early Edition, Aug. 25, 2008, 6 pages.

Application and File history for U.S. Appl. No. 16/113,707, filed Aug. 27, 2018. Inventors: Donaldson.

Application and File history for U.S. Appl. No. 13/961,422, filed Aug. 7, 2013. Inventors: Donaldson.

Application and File history for U.S. Appl. No. 15/448,680, filed Mar. 3, 2017. Inventors: Donaldson.

Application and File history for U.S. Appl. No. 16/401,692, filed May 2, 2019. Inventors: Donaldson.

Application and File history for U.S. Appl. No. 14/581,339, filed Dec. 23, 2014. Inventors: Donaldson.

Application and File history for U.S. Appl. No. 16/015,586, filed Jun. 22, 2018. Inventors: Donaldson.

Application and File history for U.S. Appl. No. 17/247,466, filed Dec. 11, 2020. Inventors: Donaldson.

PERCUTANEOUS ACCESS PATHWAY SYSTEM

RELATED APPLICATIONS

This application is a continuation of application Ser. No. 16/948,640, filed Sep. 25, 2020, now U.S. Pat. No. 11,406,809, issued Aug. 9, 2022, which in turn is a continuation of application Ser. No. 16/113,707, filed Aug. 27, 2018, now U.S. Pat. No. 10,814,119, issued Oct. 27, 2020, which claims the benefit of U.S. Provisional Application No. 62/562,183, filed Sep. 22, 2017, both of which are hereby incorporated by reference herein.

U.S. patent application Ser. No. 13/961,422, filed Aug. 7, 2013 and entitled Method and Device for Simultaneously Documenting and Treating Tension Pneumothorax and/or Hemothorax and U.S. patent application Ser. No. 14/581,339, filed Dec. 23, 2014 and entitled Percutaneous Access Pathway System and Method, both having one of the same inventors as the present application, and both are hereby incorporated by reference herein.

This invention was made with government support under contract W81XWH-17-C-0211, "PleuraPath Quick-Connect Chest Tube System," awarded by U.S. Army Medical Research Acquisition Activity (USAMRAA). The government has certain rights in the invention.

FIELD OF THE INVENTION

The present disclosure relates generally to the field of medical devices, and more particularly, to devices and methods for forming and/or maintaining a percutaneous access pathway in a patient's body.

BACKGROUND OF THE INVENTION

A wide variety of diagnostic and therapeutic procedures involve the introduction of a device through a natural or artificially created percutaneous access pathway in a body of a patient. One of the general objectives of access systems developed for this purpose is to minimize the introduction of infectious organisms from the skin or external environment into the body, while allowing for diagnostic and/or therapeutic procedures that require access into the body.

Tube thoracostomy (i.e. the percutaneous placement of a chest tube into the pleural space) is an example of one type of procedure that requires an artificially created pathway. There are several possible reasons for needing to place a chest tube into the pleural space (the space between the visceral pleura covering a lung and the parietal pleura covering the inside of the chest wall). These reasons may be medical or traumatic in nature, and include the drainage of a wide range of fluids, such as blood (hemothorax), air (pneumothorax), pleural effusion, serous fluid (hydrothorax), chyle (chylothorax), and pus (pyothorax). However, a chest tube can fail to remove all the air and/or fluid in some patients due to various factors, such as, for example, tube kinking, clogging, and/or poor initial placement. Retained air and/or fluid place patients at risk for serious infection (e.g. empyema) and underinflated lung (i.e. trapped lung), which can lead to longer stays in the hospital, extensive medical costs, and even death.

A number of methods for performing tube thoracostomies are disclosed in U.S. Pat. Nos. 9,616,203 and 10,046,147 to Donaldson, previously incorporated herein by reference. However, despite these improvements all existing methods still have a significant infection risk when placed outside of a sterile operating room, as the procedure requires a very large sterile field (around 3 ft×2-3 ft). This is because the sterile chest tube is long and floppy and touching anything nonsterile can introduce infection. The need to maintain this large field adds time to the procedure and makes it more difficult to perform outside of the operating room (e.g., on the battlefield, in the out-of-hospital arena, in the emergency department), while likely contributing to chest tube associated infections.

Additionally, the portion of the chest tube outside the body immediately becomes unsterile after finishing the procedure. Thus, the chest tube should not be moved further into the patient after initial placement even if it was inserted too shallowly or becomes dislodged. For example, if retained hemothorax is later identified (e.g. on chest x-ray or computed tomography), the chest tube cannot be easily and safely moved to target the buildup. Instead, either a new chest tube must be placed or a new sterile field needs to be reestablished and a second nearly-complete procedure performed to move the tube to the pocket of retained blood, promoting additional infection risk. This same problem also occurs if the initial chest tube placement was too shallow or if it becomes dislodged or clogged.

Under the current standard of care, due to its significant morbidity and mortality, a retained hemothorax is treated instead with early Video-Assisted Thoracoscopic Surgery (VATS). VATS is a type of thoracic surgery performed by a thoracic (sub-specialty) surgeon using a small video camera introduced into the patient's chest, frequently via surgical trocar, to directly break up and remove the retained hemothorax. However, VATS is expensive, requires general anesthesia with a specialized endotracheal breathing tube, and cannot be used in certain circumstances (e.g. a patient with spinal injuries or marginal lung function). Thus, a method of preventing or removing retained hemothoraxes that precludes VATS would be a clinical breakthrough for a great number of patients.

Similarly, prior art describes advances that have resulted in the ability to perform minimally invasive surgery in many locations throughout the body via one or more surgical ports (sometimes known as a trocar or introducer set). Such ports are used for many types of surgery (e.g. VATS, laparoscopic surgery in the abdomen, neurosurgery). A typical port consists of an obturator (a blunt or sharp internal puncturing rod); a cannula (e.g. a stiff plastic tube); and a pierceable seal (e.g. duckbill valve). Once placed in the body, the obturator is removed and the remaining device serves as a portal for the subsequent placement of other instruments (e.g. scissors, graspers, staplers). The pierceable seal (e.g. duckbill valve) of such ports are directed to keep air within the body, for use with insufflation for visualization. There are numerous additional advantageous characteristics for different kinds of trocars that are well known in the art. For example, newer trocars may utilize a flexible and expandable cannula that is then dilatated by an obturator or other equipment after placement.

However, although such minimally invasive ports greatly benefits patients by minimizing surgical trauma, such procedures are primarily performed in an operating room that maintains functional sterility externally around the patient while the surgeon is dressed in sterile attire (e.g. sterile gloves, gown). Sterile equipment is thus handled by the surgeon in full sterile attire before placement through a surgical port into the patient, during which the surgeon continues to manipulate it while wearing sterile protective gear. However, this traditional setup means that such procedures are less amenable to performance outside the operating room (e.g. emergency department, intensive care unit) where sterility of the operator and their equipment is more difficult to maintain. Additionally, if there is need for repeating the procedure or adjusting a drain or other device left within the patient, the patient must normally return to the operating room where a full sterile setup is reestablished.

The literature discloses various additional known methods and devices for forming and/or maintaining a percutaneous access pathway.

For example, U.S. Pat. Pub. No. 2007/0038180 to Sinha et al. describes a chest tube insertion gun that pushes the chest tube through the chest wall using a sharp trocar. This is a mechanical version of the trocar method and it still has the noted drawback of potential injury to underlying organs from the sharp trocar.

U.S. Pat. Pub. Nos. 2006/0025723 to Ballarini; U.S. Pat. No. 5,897,531 to Amirana; and, 2006/0025723 A1 to Ballarini describe devices for securing a chest tube to the external skin of a patient. U.S. Pat. Pub. No. 2008/0103451 to Schaefer and U.S. Pat. No. 4,221,215 to Mandelbaum, U.S. Pat. No. 5,215,531 to Maxson et al., and U.S. Pat. No. 5,263,939 to Wortrich are other similar examples of external anchoring mechanisms for percutaneous tubes. Similarly, U.S. Pat. No. 6,638,253 to Breznock describes a chest tube with an internal check valve, distal holes that open using a central rod, and a balloon holding the device inside the patient. Although this anchors the tube to the patient from the inside, it does not reduce the chance of iatrogenic injury or infection.

Several prior works describe the placement of percutaneous access pathway ports into the body to allow entrance into inner cavities. Chinese Pat. No. 1,756,513B and U.S. Pat. Nos. 7,811,293 and 7,842,058 to Simpson et al. describe a cutting gun that inserts a port for chest tube placement. After port placement, a chest tube can be inserted into the body thought the port opening. U.S. Pat. No. 6,517,519 B1 to Rosen et al. describes a trocar for rapid chest tube insertion However, none of these address the need to minimize a sterile field outside of the operating room, while allowing for later manipulation by a non-sterile user.

Other transcutaneous ports include mechanisms for reduced infection risk and pain. For example, U.S. Pat. No. 3,777,757 to Gray et al. describes an inflatable chest tube port to increase patient comfort. Others include U.S. Pat. No. 3,789,852 to Kim et al.; U.S. Pat. No. 5,545,179 to Williamson, IV; and U.S. Pat. No. 4,767,411 to Edmunds and U.S. Pat. Pub. No. 2004/0078026 to Wagner. Further, U.S. Pat. Nos. 8,518,053; 8,430,094; and 7,824,366 and U.S. Pat. Pub. Nos. 2009/0205646; 2010/0170507; and 2009/0205651 to Tanaka, et al., as well as U.S. Pat. No. 8,062,315 to Aster et al. all describe transcutaneous ports placed to specifically establish a pneumostoma (a transcutaneous hole terminating inside the lung tissue itself, as opposed to the pleural space around the lung in tube thoracostomy). However, these do not significantly mitigate the limitations of transcutaneous port insertion.

Prior works describe transcutaneous access via the use of expanding catheters or other dilatational devices. For example, U.S. Pat. Pub. No. 2013/0131645 to Tekulve describes a chest tube that has an internal diameter that inflates and deflates to remove clogged blood. However, this is only an internal mechanism and does not significantly change the external diameter of the chest tube. U.S. Pat. Pub. Nos. 2007/0021768 and U.S. Pat. No. 8,092,481 to Nance et al. describe an expandable tube for nephrostomy procedures, however it has no improved sterility mechanism and does not have other benefits related to tube thoracostomy. Other examples include U.S. Pat. Pub. Nos. 1993/005183464, U.S. Pat. Nos. 5,431,676, and 6,325,812 to Dubrul et al.; U.S. Pat. No. 6,162,236 to Osada; U.S. Pat. No. 7,892,170 to Moreno et al.; U.S. Pat. No. 7,896,897 to Gresham et al.; 2004/0049222 to Schaeffer et al.; 2004/0199121 to Wenchell et al.; 2006/0212062 to Farascioni; 2005/0203565 to Rethy et al.; 2006/0041270 to Lenker et al.; U.S. Pat. No. 8,257,251 to Shelton, I V et al.; U.S. Pat. No. 8,795,326 to Richard; 2003/0216770 to Persidsky et al.; and, 2009/0030375 to Franer et al. However, none of these are part of systems that minimize the sterile requirements of the user in a non-operating room environment.

Other examples include U.S. Pat. Pub. No. US 2009/0318898 and U.S. Pat. No. 8,403,913 to Dein that describe a chest tube capable of deflation to provide easier removal from the body and U.S. Pat. No. 8,128,648 to Hassidov et al. that describes a gun with an expandable cutting trocar for use in placing a chest tube. However, neither provides an improved port for transcutaneous access into the body or an improved method for maintaining sterility during placement.

U.S. Pat. Pub. No. 2011/0152874 to Lyons describes a balloon dilatational chest tube apparatus and method that partially reduces the number of steps needed in the traditional Seldinger technique. A balloon distal to a chest tube inflates and then deflates so that the chest tube can be advanced into the dilated space (and over the deflated balloon). This work still is limited in that the chest tube must be pushed through chest wall tissue over the deflated balloon; there is no reusable port for easier changing of clogged or misplaced chest tube(s), and it does not significantly improve the sterility of the tube thoracostomy procedure.

The prior art contains works related to the placement of ports and/or trocars into a patient for surgery (e.g. Video-Assisted Thoracoscopic Surgery (VATS), thoracic surgery, laparoscopic surgery, single-port access surgery, multi-port access surgery, vascular surgery, neurosurgery). Examples include U.S. Pat. No. 5,489,290 to Furnish; U.S. Pat. No. 5,490,843 to Hildwein et al.; U.S. Pat. No. 5,562,677 to Hildwein et al.; U.S. Pat. No. 5,776,110 to Guy et al.; U.S. Pat. No. 5,830,191 to Hildwein et al.; U.S. Pat. No. 7,776,003 B2 to Zauner; 2009/0209913 A1 to Ferrari; 2010/0249694 A1 to Choi et al.; and, US 2011/0201883 A1 to Cooper et al. However, all these devices are optimized for use in a sterile operating room environment and/or equipment manipulation while wearing sterile gloves.

The prior art also contains works relevant to infection reduction and the improvement of sterility during the establishment of a percutaneous access pathway. There are examples of flexible sheaths to maintain sterility around percutaneous catheters. For example, U.S. Pat. No. 5,807,341 to Heim; U.S. Pat. No. 6,605,063 to Bousquet; U.S. Pat. No. 5,662,616 to Bousquet; and U.S. Pat. No. 4,392,853 to Muto and U.S. Pat. Pub. No. 2012/0191044 to Koike describe such sheaths around venous catheters. Similarly, U.S. Pat. No. 5,242,398 to Knoll et al.; U.S. Pat. No. 7,789,873 B2 to Kubalak et al.; and U.S. Pat. No. 3,894,540 to Bonner, Jr. describe such sheaths around urinary catheters. U.S. Pat. No. 4,767,409 to Brooks and U.S. Pat. No. 5,215,522 to Page et al. describe such sheaths around central venous pressure catheter and endotracheal tube suction devices, respectively. U.S. Pat. Nos. 5,336,193 and 5,429,608 to Rom et al. and U.S. Pat. Pub. No. 2008/0125750 to Gaissert describe bags to minimize the provider's exposure to bodily fluids during chest tube removal. However, such flexible sheaths are not optimally designed to maintain sterility in conjunction with the reusable connection to an inserted percutaneous access port.

Another example is U.S. Pat. No. 7,244,245 to Purow that describes a rigid sheath device to maintain chest tube adhesion to the chest wall and prevent pneumothorax. However, this follows standard chest tube insertion techniques and provides minimal reduction of infection.

Finally, U.S. Pat. Nos. 6,905,484 and 7,135,010 to Buckman et al. describe a military chest tube over a trocar in a sterile package. However, the works do not describe a mechanism for maintaining sterility within the system after puncturing the packaging with the chest tube, as the tube then becomes exposed to the outer environment. Additionally, there is no easily reusable percutaneous access pathway established.

Regardless of use, the transcutaneous access devices and methods of the art have not before provided for an optimized device for accessing a body cavity that allows for repeated access. As such, there is a need for a device and method to do so.

Each of the patents and published patent applications mentioned above are hereby incorporated by reference.

SUMMARY OF THE INVENTION

The present invention overcomes and substantially alleviates the deficiencies in the prior art by providing improved devices and methods for forming and/or maintaining a percutaneous access pathway. Under various embodiments, the initial percutaneous access pathway is formed via different methods and devices, which include the aforementioned techniques noted as background of the present invention that have been incorporated by reference. The provided assembly substantially reduces the possibility of iatrogenic infection while accessing and/or re-accessing a body space.

Under many embodiments, the percutaneous access pathway includes a catheter (e.g. a trocar cannula) irreversibly attached to a port that allows a serial, reversible connection to one or more attachment devices. In many embodiments, the access pathway port allows an entrance to the catheter to be reversibly blocked by a lockable and non-pierceable port, thus preventing air and/or infection from entering the body cavity. This contrasts with a typical trocar seal (e.g. large duckbill valve), which is meant to keep insufflated air from escaping the body cavity, while being non-lockable and further easily pierceable by the introduction of equipment going through the seal to enter the body cavity.

In many embodiments, the access pathway port contains a mobile pathway (e.g. through a cylinder, sphere, ball, ball-valve mechanism), valve (e.g. ball-valve mechanism), door, and/or tumbler that moves (e.g. rotates, slides) to block or allow access to the attached catheter and thus body cavity. In some embodiments, movement of the mechanism is caused manually by the operator (e.g. button, lever, switch, nob) and in others is caused automatically by connection of an attachment device to the port. In many embodiments, the access pathway port when in its closed position is lockable in a manner to prevent easy opening when an attachment is not connected. In many embodiments, the access pathway port when in its closed position is not easily pierceable. However, in some embodiments the access pathway port, attachment, and/or catheter does contain one or more additional pierceable barriers (e.g. duckbill valve, rubber, film, stopper) to keep air in or out of the body when the port is open.

In many embodiments, only the connection of an attachment device to the access pathway port allows the access pathway port to open, thus preventing air and/or infectious material from entering the port and body when an attachment device is not attached. In these embodiments, the attachment device thus functions as a key to open the locked port. When the access pathway port is closed, it is automatically or manually locked so that it cannot be easily opened without connection to an attachment device. Additionally, when closed, the port cannot easily be pierced, unlike a typical trocar seal.

In many embodiments, the proximal portion of the closed port is easily cleanable by swab, liquid, or other means, so that the portion that will connect to an attachment device may become functionally sterilized before doing so (e.g., if the port has been exposed to a non-sterile environment). For example, in many embodiments, the device forms a system of components that maybe interchanged, with multiple attachments that can connect to an inserted port. When the user first places the port, it is fully sterile from its packaging and an attachment can be immediately connected at that time. Should the user later remove that attachment, the patient may have only the port in for some time (e.g. a trial of cure to see if there is a return of pneumothorax for a patient with a chest tube placed for that indication). Afterwards, the external portion of the port may be contaminated. If there is need for reconnection of a new attachment (e.g. failure of the trial of cure), then some or all of the external portion of the port may easily be sterilized (e.g. swabbed) before a new attachment is connected to the port.

In many embodiments, when the access pathway (i.e. catheter and port) is connected to an attachment device, an unlocked and opened port allows a direct connection from the body, through the access pathway, to the attachment device. Under some embodiments, the access pathway port connection uses a quick connect type mechanism to expedite attachment and simplify the procedure. In some embodiments, at least part of the attachment device (e.g. internal equipment component) then enters the body via the established and open access pathway.

Many of the embodiments of the present invention contain one or more attachment devices that can connect to the port. In many embodiments, the device includes a system that includes a universal access port that can serially connect to multiple different types of attachment devices, each with its own utility and purpose (e.g. each with different internal equipment components). Thus, after universal access port placement, the user can connect to it and exchange one or more different attachment devices, depending on clinical need, without having to exchange the port.

In many embodiments, the attachment device has a mechanism to prevent contamination of any surfaces that should remain functionally sterile during use (e.g. those that will be entering the body, those that could contaminate a component that will be entering the body) when the attachment is not connected to the port. In some embodiments, this prevention mechanism is a cap that can be removed from the distal end of the attachment device before connection to the port. In other embodiments, this prevention mechanism is disengaged manually by the operator manipulating a mechanism on the attachment device (e.g. via a button, lever, switch) that removes a barrier before, during, and/or after connecting the attachment device to the port. In some embodiments, this prevention mechanism is removed automatically by the attachment of the access pathway port to the attachment device and/or insertion of part of the attachment device (e.g. internal equipment component). In some embodiments, the mechanism to remove this prevention mechanism is combined with or related to a mechanism for opening the port itself. In some embodiments, this prevention mechanism is irreversible (e.g. foil cap removal) and in others it is reversible (e.g. movable door).

In many embodiments, one or more attachment devices contain an external sheath to protect at least part of an internal equipment component from the external (e.g. non-sterile) environment. In some of these embodiments, the sheath is formed of flexible tubing (e.g. plastic), collapsible or foldable material (e.g. corrugated tubing), and/or bag or bag-like material (e.g., plastic bag, plastic tubing, etc.). In many of these embodiments, the internal equipment component of the attachment device can be inserted, manipulated, and/or removed by the operator while the outer sheath maintains a barrier (e.g. functionally sterile partition) between the portion of the internal equipment component device that will enter the body and the user. In many embodiments, the sheath is clear or at least partially transparent, to allow for visualization of the equipment within. In many embodiments, the attachment device can additionally be connected to external hookups that are standard for that device type. For example, in many of the embodiments wherein the internal equipment component is a chest tube, the proximal attachment device end allows a functional connection to a standard chest tube drainage and/or suction system.

The internal equipment component of the attachment device varies by embodiment with examples including one or more of the following: chest tube, other tube or catheter, pigtail catheter, surgical equipment, endoscope, video-assisted thoracoscopic surgery device, irrigation, suction, irrigation and suction loop, mechanical agitator, and/or other surgical instrument. Other embodiments include any equipment used for Video-Assisted Thoracoscopic Surgery (VATS), thoracic surgery, laparoscopic surgery, single-port access surgery, multi-port access surgery, and/or neurosurgery. Under various embodiments, the internal equipment component is a conventional, endoscopic, and/or robotic thoracic instrument and/or laparoscopic instrument (e.g. one or more single-port access surgery devices, cutters, forceps, scissors, staplers, probes, dissectors, hooks, retractors, sponge-holding forceps, biopsy forceps, biopsy cannulas, staple-transection devices, electric knifes; suction devices, sutures, and/or retractors). Various embodiments additionally include grasping and/or dissecting forceps with various properties and sizes (e.g. atraumatic, curved, single-action, double-action, short, long, fine tip, serrated, toothed, fenestrated, claw grasping forceps, with lock, without lock, with fine cross-cut toothing, angled, fine pyramid-shaped toothing, fenestrated, with fine cross-cut toothing, slimline, jaw throat with wavy tooth edge, grasping surface with fine cross-cut toothing, large distal grip jaws with fine cross-cut toothing, atraumatic clip, with one tooth, plate-shaped, distal cross-cut toothing with jaw throat, biopsy, with pins, without pins, severing, pointed spoon, extracorporeal knot applicator, insulated, spring jaws, triangular, pike-mouth, double-spoon, punch, Babcock, Maryland, Mixter, Dolphin, Debakey, Petelin). Various embodiments also include scissors (e.g. micro, straight, hook, serrated, pull rod, sheath, Metzenbaum). Other embodiments also include neurosurgical equipment (e.g. ventriculostomy tube, intracranial pressure monitor, intracranial oxygen monitor, external ventricular drain, device to drain intracranial hemorrhage, other ventricular shunt). In many embodiments, the internal equipment component is at least partially enclosed within a sheath, although in some embodiments no sheath is utilized (e.g. Heimlich valve attachment).

By way of exemplification, in one embodiment, the internal equipment component of the attachment device is a chest tube covered by a sheath over most of its length. After removal of a cap over its distal attachment end, the attachment device can be connected to the access port. However, it should be clear that embodiments include any standard drainage and/or surgical equipment that is amenable to being placed within a sheath and can be inserted through the access port. The invention is not limited to only a chest tube or the other internal equipment components set forth herein for purposes of exemplification.

In many embodiments, one or more attachment devices contain a reversible locking mechanism (e.g. equipment locking mechanism) to ensure that the internal equipment is not inserted into the body until the operator wishes it to do so and/or stays in the desired location once inserted in the body (e.g. holding a chest tube at the desired length within the pleural cavity). Under some embodiments, the equipment locking mechanism is a piece of plastic with a hole cut out for a piece of equipment to move within that is biased (e.g. by spring, band, and/or its own material) upward and thus holds the internal equipment in place when not depressed, but allows it to move into or out of the patient when depressed. In other embodiments, the equipment locking mechanism is actuated by rotating the lock and thus compressing one or more O-rings against a compression piece, causing the O-ring to hold the internal equipment component in place. In some embodiments, an equipment locking mechanism utilizes other mechanisms to reversibly hold the internal equipment component at the desired position within the body such as, for example, a clamp, tie, hose clamp, screw/band clamp, worm gear, Jubilee Clip, Marman clamp, spring clamp, wire clamp, ear clamp, compression fitting, push-fit fitting, swage fitting, clamp fitting, crimp banding, and/or t-bold clamp. In some embodiments, the attachment device has no equipment locking mechanism (e.g., Heimlich valve attachment).

In many embodiments, one or more attachment devices of a full system have no sheath and/or internal equipment component. For example, in some embodiments the access pathway port reversibly connects to an attachment device with a check valve (e.g. Heimlich valve) that allows air to release from, but not to enter, the body. As the check valve is not inserted into the body, there is no need for a sheath for this attachment device. Under some embodiments, this check valve attachment can then be reversibly exchanged on the inserted port with another attachment device that does contain a device partially covered within a sheath (e.g. chest tube), to provide system benefits.

In many embodiments, the access pathway anchors, stabilizes, and/or secures the percutaneous access pathway to the body (e.g. via securing the access pathway port to the skin and/or deeper structures). Examples include stabilization through sutures, staples, glue, gum, and/or tape; tension from an expanded catheter within the body wall; adhesive that holds the catheter, port, and/or a larger stabilization pad onto the skin; and/or, expansion of one or more balloon(s) within the body cavity, within the percutaneous access pathway, and/or externally. In many embodiments, the aforementioned means provide the added benefit of preventing air and/or infection from entering the body from around the outside of the catheter (e.g. through space between the outside of the catheter and the surgical incision). In various embodiments, the catheter and/or port is anchored to make the percutaneous access pathway perpendicular to the skin, at a non-perpendicular angle (e.g. to facilitate internal chest tube placement or surgical access), and/or adjustable so as to allow movement to a desired angle.

Under some embodiments, the catheter is a stiff tube that is not readily deformable (e.g. a plastic trocar cannula). Some of these embodiments additionally include an obturator (e.g. a blunt or sharp internal puncturing rod) and/or a pierceable seal (e.g. duckbill valve), as are known in the art for surgical trocars. Under other embodiments, the catheter is flexible, so that a smaller cross-sectional diameter catheter may be placed in the body before later expansion by dilation with a specific dilation tool and/or by dilation from part of an attachment device entering the catheter through the external port (e.g. internal equipment component). For example, an operator can place an access pathway with a flexible catheter that is initially contracted to provide a narrow cross-sectional diameter, through a small incision into a body cavity. Then, an attachment device can be connected to the access pathway port and, when an internal portion of the attachment device (e.g. chest tube, other internal equipment component) that is of larger diameter is advanced, the catheter will be dilated to allow the passage of said internal equipment component into the body cavity. Under various embodiments, the flexible catheter is formed of a plastic deformable tube, expandable metal (e.g. stent, mesh, rolled material, reinforced wires), expandable catheter filled with gas (e.g. air) or fluid (e.g. normal saline), and/or, braided sheath (e.g. nylon, PTFE, PFA). Various embodiments include the combination of the aforementioned materials (e.g. a braided sheath covered by an expandable plastic tube).

In some embodiments, the catheter and/or port is covered partially or fully with additional material(s) that can provide additional benefits when in contact with the body tissue. Examples include means to increase and/or decrease the cross-sectional area of the catheter; to reduce friction and/or the chances of tissue being pinched in the underlying catheter or mechanism; to decrease the chances of infection (e.g. antimicrobial properties); and/or to have drug-releasing properties (e.g. anesthetic or other anti-pain medications). Under some embodiments, there is no catheter and the port is placed directly over an incision into the body, with the port allowing access to the underlying potential or maintained pathway into the body. In some embodiments, the catheter and port reversibly combine, to allow for disassembly and leaving the catheter in the body while removing the port, if so desired.

In some embodiments, one device fits all patients. In others, part or all of the device is differently sized for different subgroups so that the appropriately sized device can be chosen for different subgroups based on, for example, weight, age, gender, length, pre-determined size categories (e.g. Broselow scale), and/or other indicators. For example under some system embodiments, the port and portion of the attachment device that connect to it are universal, while the access pathway catheter may come in more than one length (e.g. small, medium, large) and there are multiple different attachment device options and sizes (e.g., drainage tube diameters). This allows any attachment device to be used with a placed port, but the user may choose different catheter lengths based on the patient (e.g. patient size) and attachment based on clinical need (e.g. chest tube diameter size). Under various embodiments, differently sized components come together in a kit, with means for determining proper sizing. In one embodiment, the catheter may be cut to length by the user prior to insertion.

Under different embodiments, different portions of the device are disposable and/or non-disposable. In some embodiments, the invention is inexpensively manufactured with all of it designed to be disposed of after a single use. Parts may be made of metal or plastic or other suitable material. Under various embodiments, different parts are composed of a radio-opaque material and/or contain radio-opaque markers (e.g. chest tube with radio-opaque line). Under various embodiments, the device may be packaged as a system with a port, attachment device, and/or insertion equipment all coming together, while in others the device components (e.g. port, attachment device) are packaged separately as individual units.

There have been illustrated and described herein methods and devices for forming and/or maintaining a percutaneous access pathway. While particular embodiments of the invention have been described, it is not intended that the invention be limited thereto, as it is intended that the invention be as broad in scope as the art will allow and that the specification be read likewise.

From the foregoing, it can be seen that the present invention provides an effective means for forming and/or maintaining a percutaneous access pathway within animals, especially humans. In various embodiments, the device is used to form and/or maintain a percutaneous access pathway into different body cavities. These include pathways into the chest (e.g. pleural cavity, heart), abdomen, retroperitoneal, cranium, trachea, abscess, artery; bladder; bone; collection of fluid (e.g. empyema, ascites, pleural, other effusion); organ; skull, trachea; vein; vessel; and/or, other body cavity. Although the example of the chest with a thoracostomy procedure placing a chest tube has at times been used to illustrate the invention, this could also similarly be, for example, the abdominal cavity with a laparoscopic procedure placing an abdominal drain (which could give the benefit of repeat laparoscopy procedures without having to place new ports and/or some of these procedures being performed outside of a standard sterile operating room). This can also similarly be used with any other surgical procedure where a reusable port for repeat procedures and/or manipulation in a non-sterile environment would be of benefit. These include, but are not limited to, insertion of a Penrose drain; pigtail catheter; tracheostomy tube; endotracheal tube; venous or arterial catheter; thoracentesis tube; paracentesis tube; abscess drainage; and/or, other catheter.

In some embodiments, the device is used to form and/or maintain a percutaneous access pathway into the cranium. This pathway can then be used to connect to and introduce at least part of an attachment device (e.g. ventriculostomy tube, intracranial pressure monitor, intracranial oxygen monitor, external ventricular drain, device to drain intracranial hemorrhage, other ventricular shunt), if so desired.

Moreover, it should also be apparent that the device can be made in varying lengths and sizes (e.g., diameters) to treat adults, children, and infants. While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, and that elements of certain embodiments can be combined with elements of other embodiments. Additional objects, advantages, and novel features of the invention will be set forth in the description which follows, and will become apparent to those skilled in the art upon examination of the following detailed description and figures. It should be understood that not all of the features described need be incorporated into a given method or device.

DETAILED DESCRIPTION OF THE INVENTION

Figure 1:
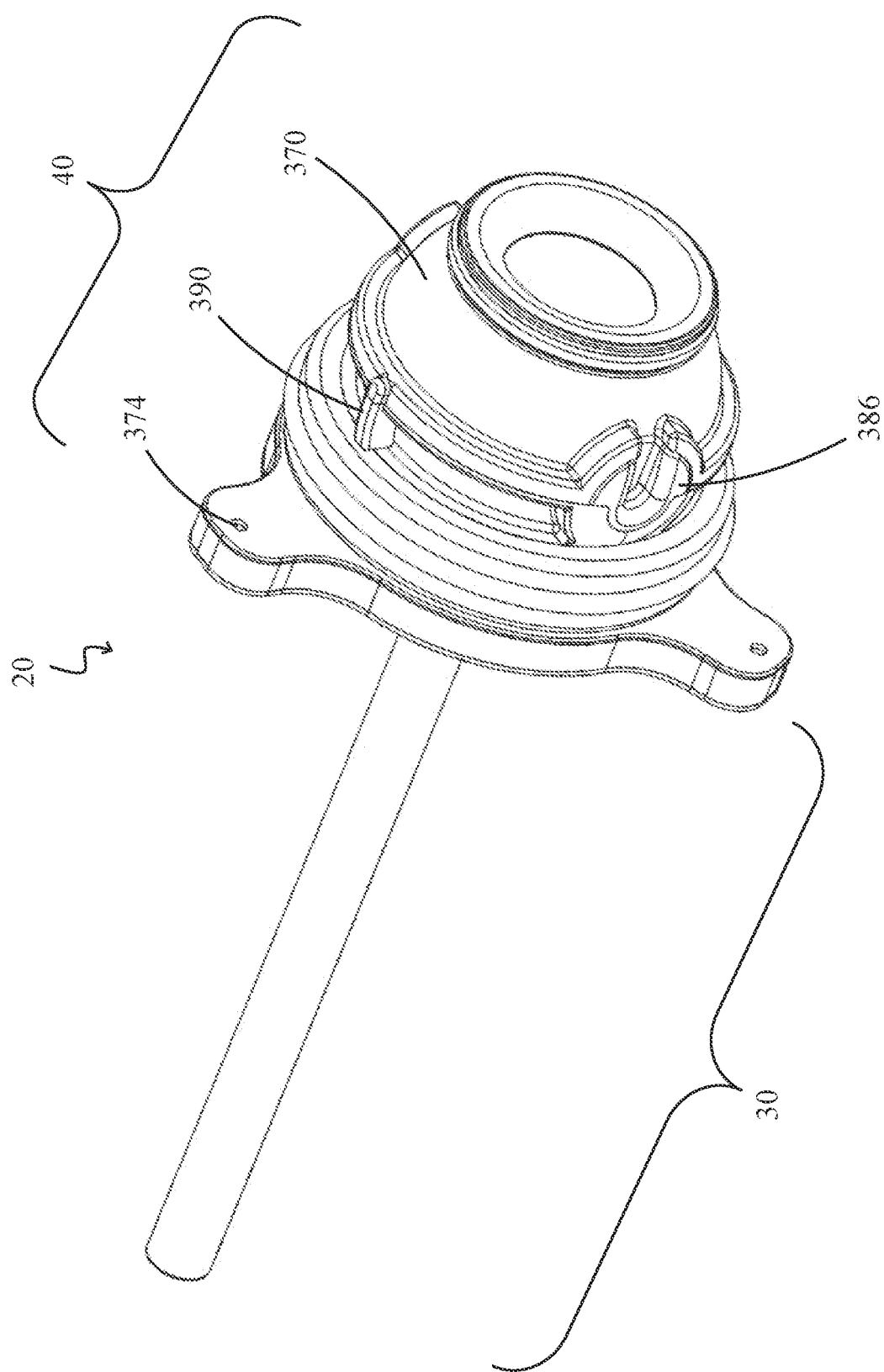
FIGS. 1-4 depict a percutaneous access pathway in accordance with an embodiment of the invention, as assembled prior to use.
Figure 2:
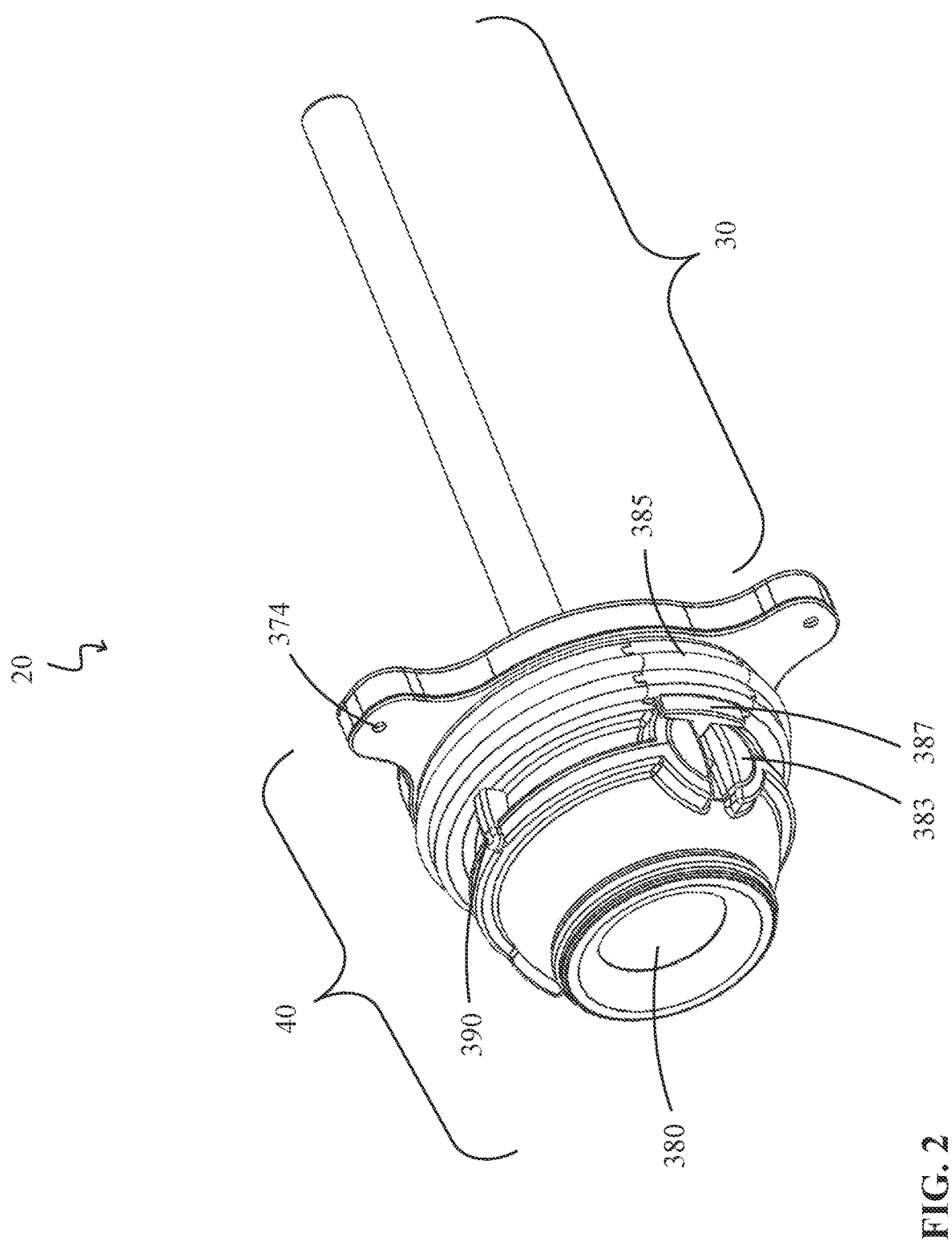
Figure 3:
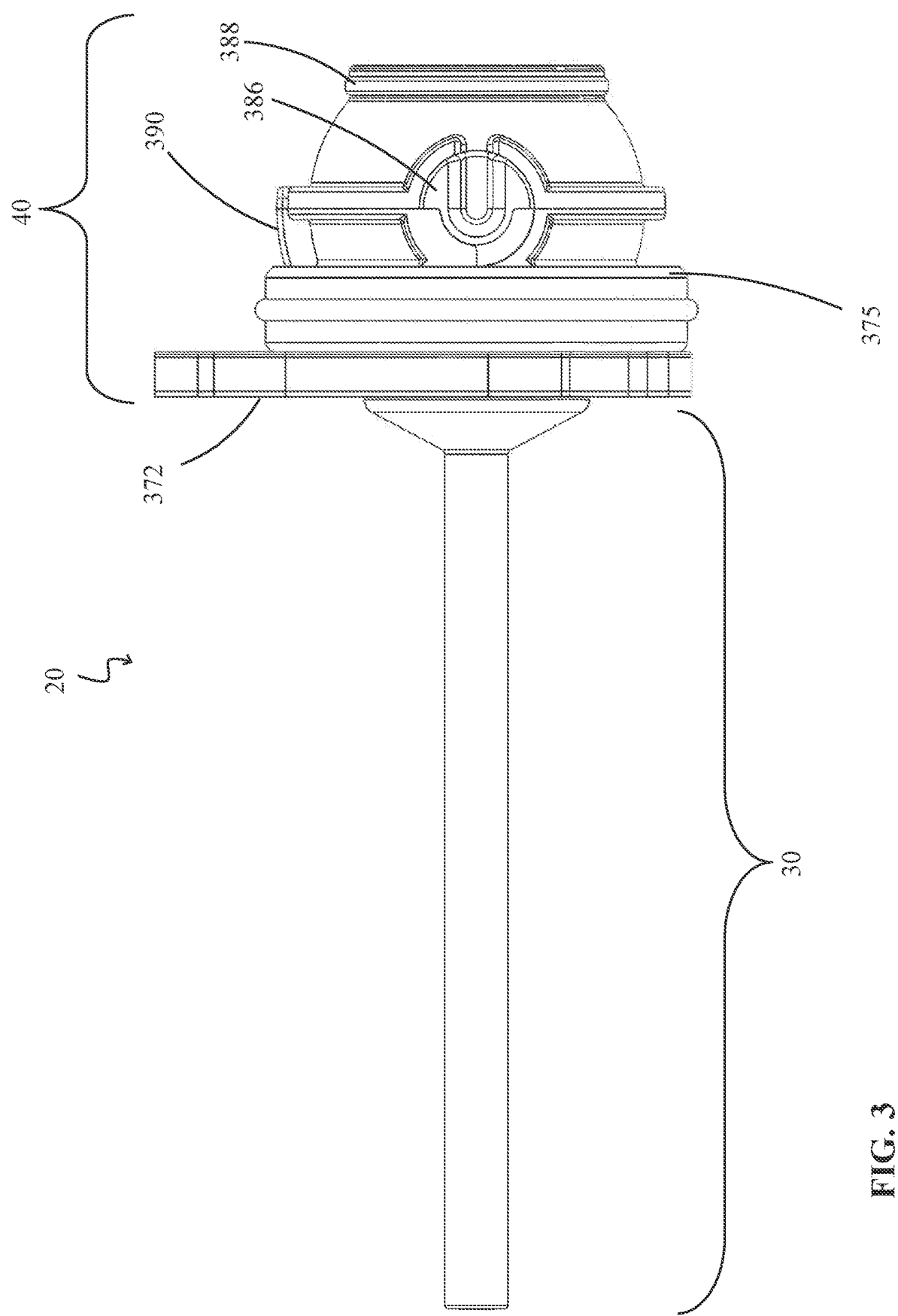
Figure 4:
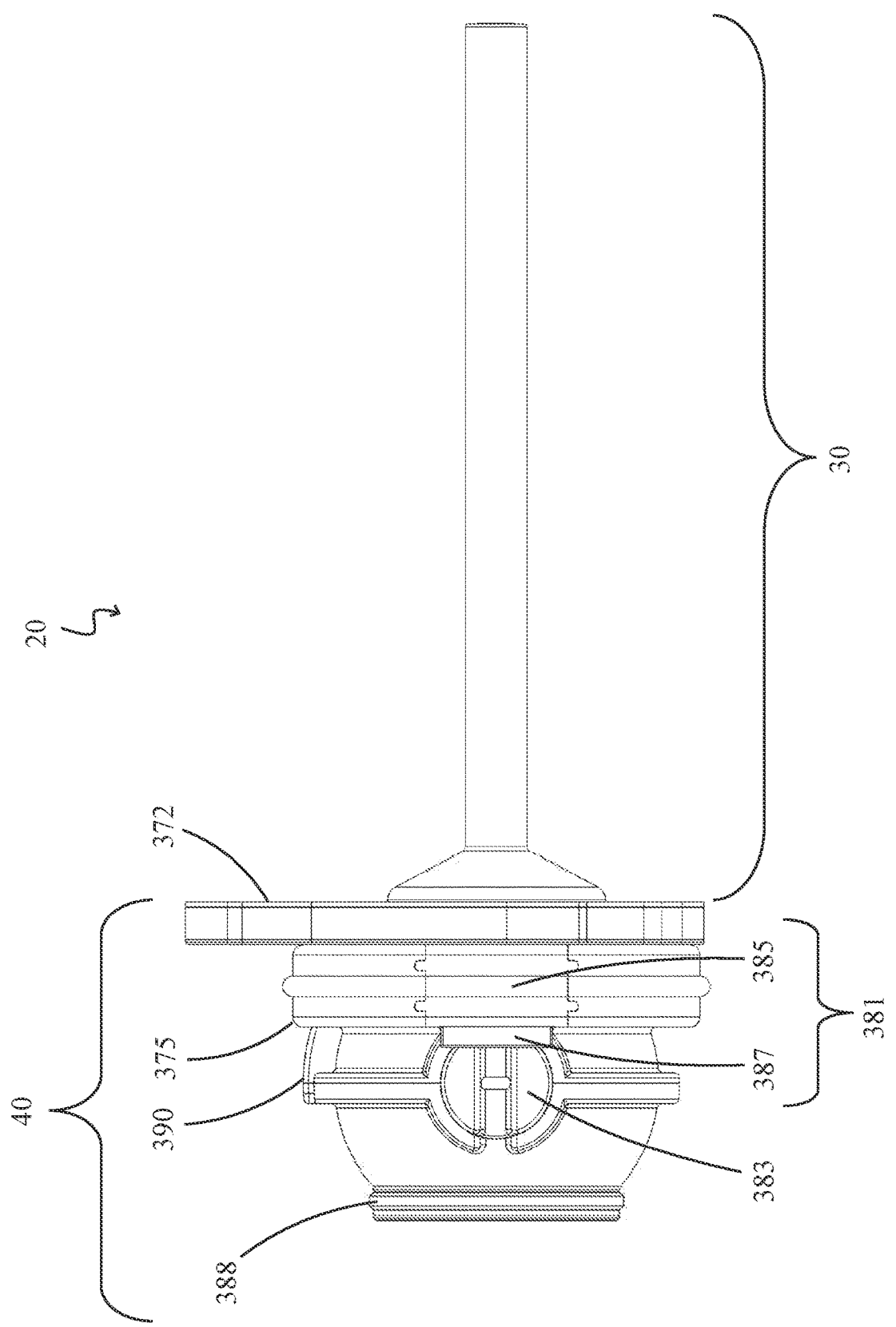
Figure 5:
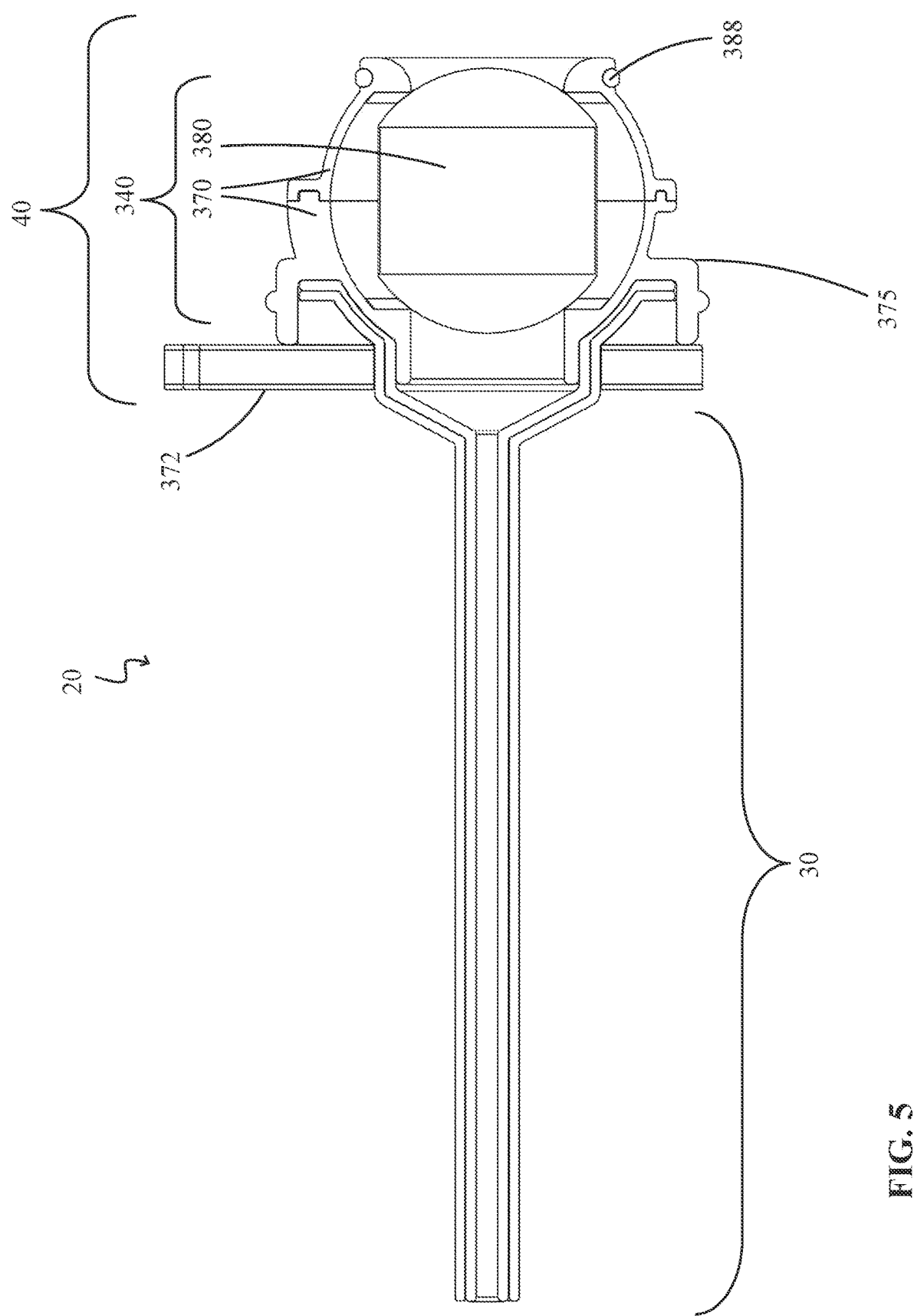
FIG. 5 is a cross-sectional view of a percutaneous access pathway in accordance with an embodiment of the invention, as assembled prior to use.

Referring to the drawings FIG. 1-20, embodiments of the present invention are illustrated and generally indicated as 10. For ease of reference, distal shall refer to the end of the device farthest away from the user/operator, while proximal shall refer to the end of the device closest to the user/operator.

FIGS. 1-5 show an access pathway 20 made up of the irreversible combination of a catheter 30 and port 40 according to an embodiment. Once the distal end of catheter 30 is placed into the appropriate body cavity (e.g. pleural cavity) through any of the aforementioned techniques, access pathway 20 can be secured to the patient by one or more of the many means of adhering devices to patient skin known in the art (e.g. tape, glue, gum, suture, staples, adhesive, etc.). In some embodiments, surface 372 of access pathway 20 contains a means for establishing an air-tight seal (e.g. adhesive, occlusive ointment) from access pathway 20 to the patient's skin. In some embodiments, holes 374 are available for securing via suture and/or staples.

An internal pathway stretching through access pathway 20 from its distal end in a body to its proximal portion in the external environment is reversibly obstructed by a non-pierceable airtight door when in its closed state by ball-valve mechanism 340, made up of port shell 370, port ball 380, and ball-valve seats (not shown). In some embodiments, an airtight seal is formed directly between port ball 380 and port shell 370, while in others the seal is obtained and/or assisted by one or more pressure or non-pressure O-rings, seats, and/or washers. Regardless, when in its closed configuration, ball-valve mechanism 340 prevents air or infection from entering the body through access pathway 20.

A locating boss 390 on the port 40, which in some embodiments is a bright or otherwise noticeable color, ensures that it will be correctly aligned for proper engagement with attachment connector 150 (see later figures). O-ring 388 forms an airtight seal with attachment connector 150 when connected. Access pathway port 40 additionally includes locking mechanism 381, made up of pin holder 385, pin 387, and a spring (not shown), which interacts with trunnion feature 383. Together, they prevent port ball 380 from opening (i.e. rotating) when ball-valve actuating mechanism 460 of attachment connector 150 (see later figures) is not connected. However, when it is attached, key 464 of ball-valve actuating mechanism 460 (see later figures) pushes pin 387 out of the groove within trunnion feature 383 to allow ball-valve mechanism 340 to rotate and thus open port 40. Disengagement feature 386 additionally prevents disengagement of access pathway port 40 from attachment connector 150 when ball-valve actuating mechanism 460 is engaged (see later figures), ensuring that attachment connector 150 cannot be removed from port 40 until ball-valve mechanism 340 is fully closed. Flange 375 helps protect the internal mechanism of attachment connector 150 from external influences once it is connected to port 40.

Figure 6:
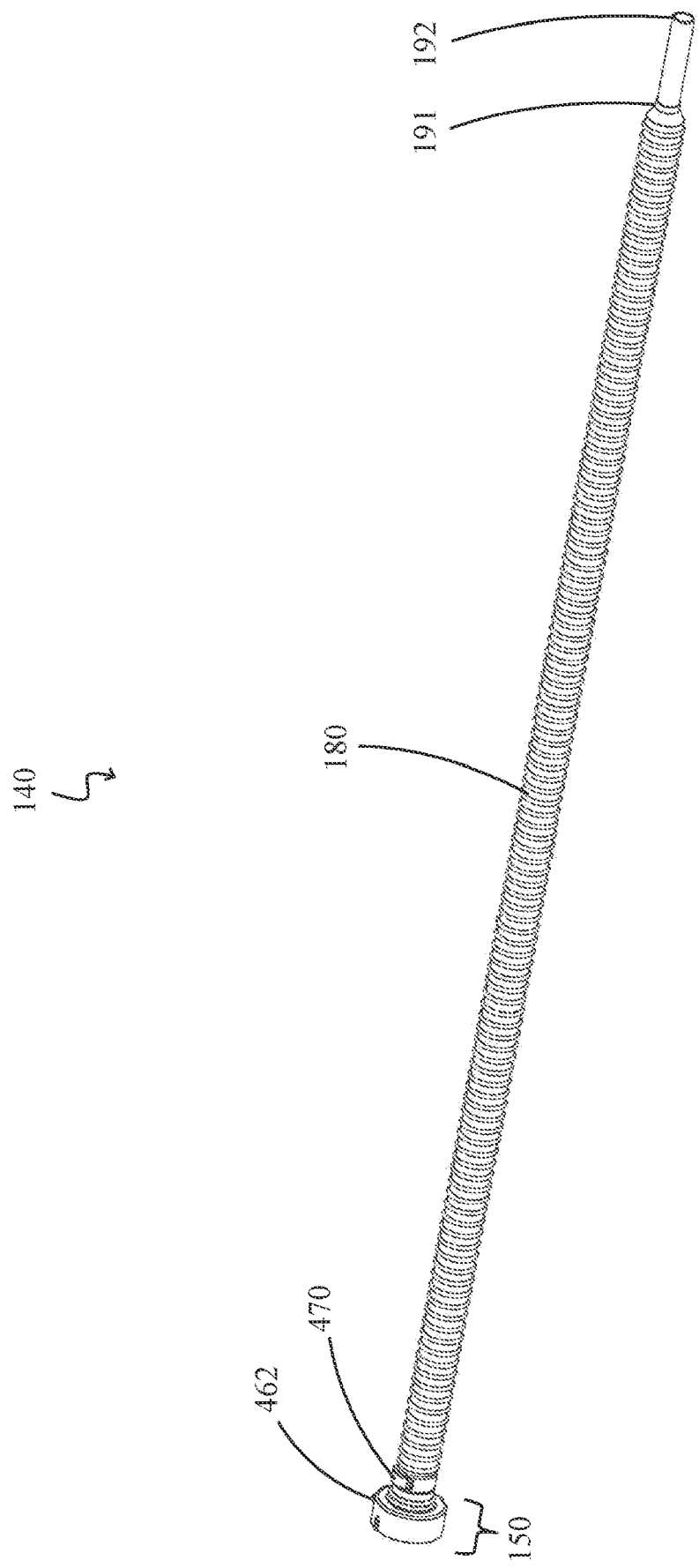
FIG. 6 depicts an attachment device containing a chest tube as an internal equipment component in accordance with an embodiment of the invention.
Figure 7:
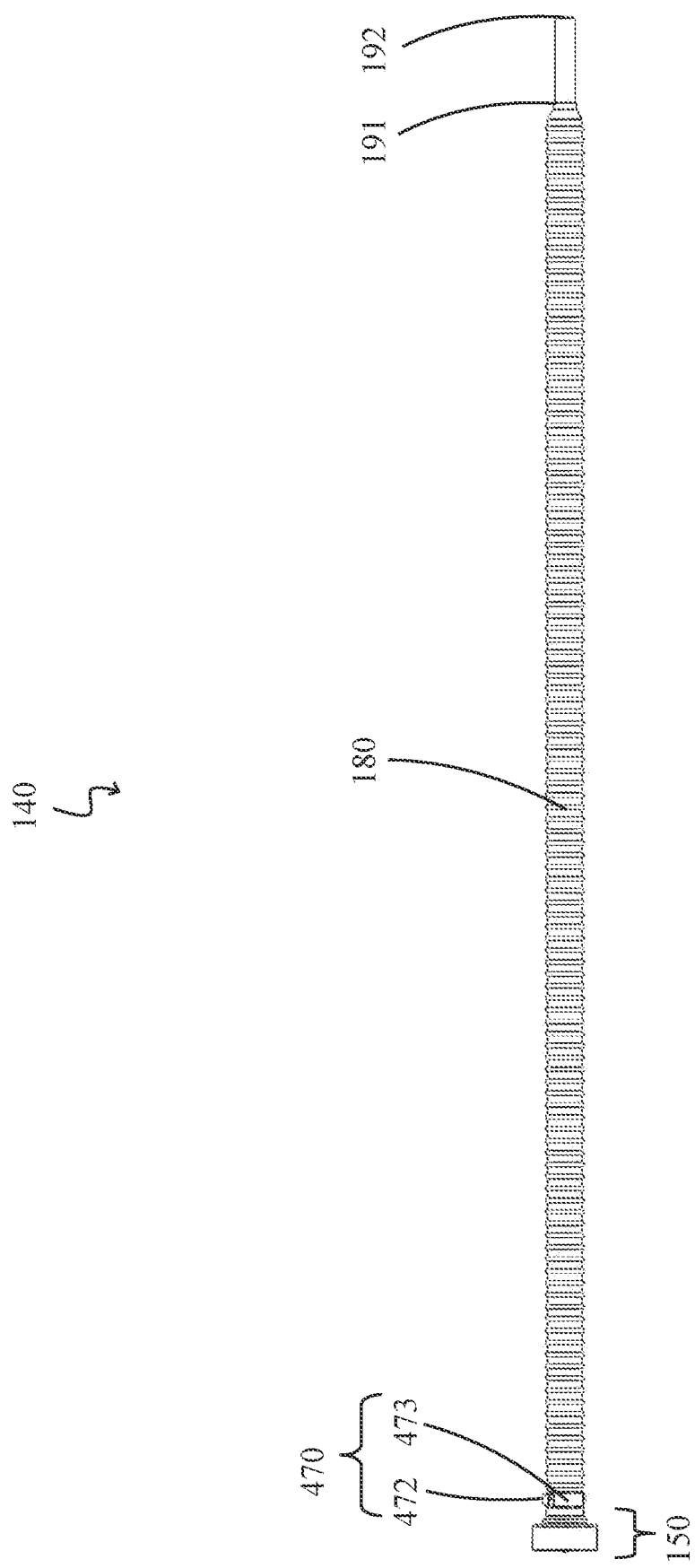
FIG. 7 is a side view of an attachment device containing a chest tube as an internal equipment component in accordance with an embodiment of the invention.
Figure 8:
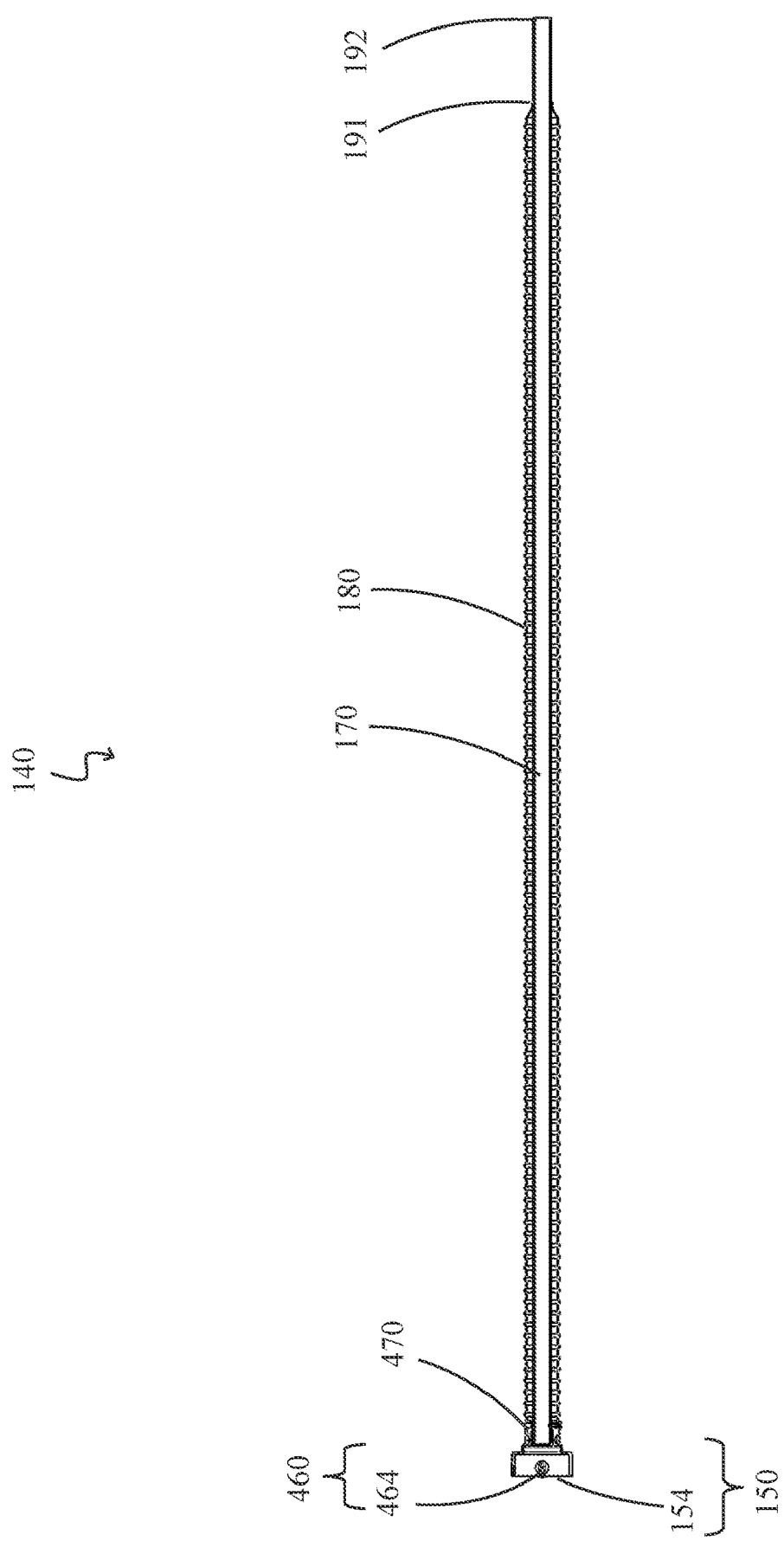
FIG. 8 is a cross-sectional side view of the attachment device of FIG. 7 in accordance with an embodiment of the invention.

Referring now to FIGS. 6-8, one embodiment of attachment 140 is shown. In this embodiment, a chest tube is used as an example of the internal equipment component. Attachment 140 includes attachment connector 150, ball-valve actuating mechanism 460, equipment locking mechanism 470, chest tube 170, and sheath 180. Chest tube 170 is at least partially covered by sheath 180 and sealed to it at connection point 191, but slides within sheath 180 and attachment connector 150 such that it can extend out of attachment exit 154 if sheath 180 is collapsed by the operator. Under some embodiments, in initial configuration attachment 140 includes a removable cap (not shown) sealing attachment exit 154 closed and/or a removable cap and/or check valve (not shown) on or around proximal end 192, which provides the benefit of enclosing an area within attachment connector 150 and sheath 180 that maintains a barrier to the external environment (e.g. for maintaining a sterile inner area before initial use). Additionally, despite outside manipulation, when attachment connector 150 is connected to access pathway 20 and the proximal end 192 is closed off or connected to a mechanism for suction (see later figures), there is a barrier between the external space and an internal space, containing at least part of chest tube 170 and connecting into the patient (e.g. for inhibiting potential infection from entering the patient). Proximal end 192 can be connected to suction or other chest tube drainage means to drain air and/or fluid from the body cavity. Attachment connector 150 contains ball valve actuating mechanism 460, which includes nob 462 (or, in other embodiments, a lever, dial, or button) and key 464. Key 464 slides into trunnion feature 383 when the attachment 140 is engaged with the access pathway port 40 and unlocks locking mechanism 381 by depressing pin 387 (see other figures). Thus, nob 462 can be turned by the operator to rotate the port ball 380 when access pathway port 40 and attachment connector 150 are connected. Attachment 140 additionally contains equipment locking mechanism 470, which includes equipment lock 472, equipment lock holder 473, and a spring 475 (shown later). Under this embodiment, to move chest tube 170 forward or backwards in reference to attachment connector 150, the user must depress tube lock 472 downward.

Figure 9:
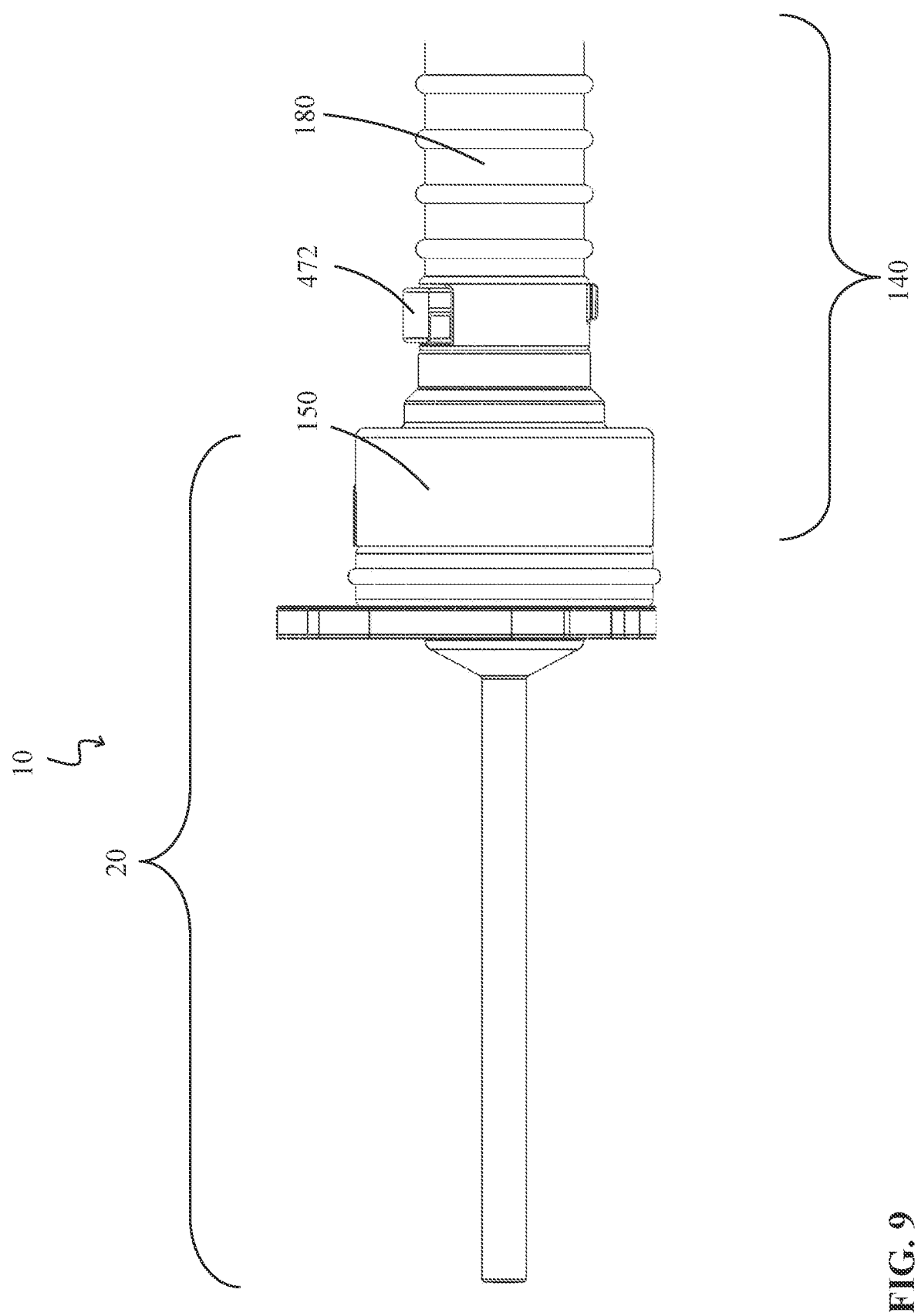
FIG. 9 is a side view of access pathway connecting to the attachment device in accordance with an embodiment of the present invention.
Figure 10:
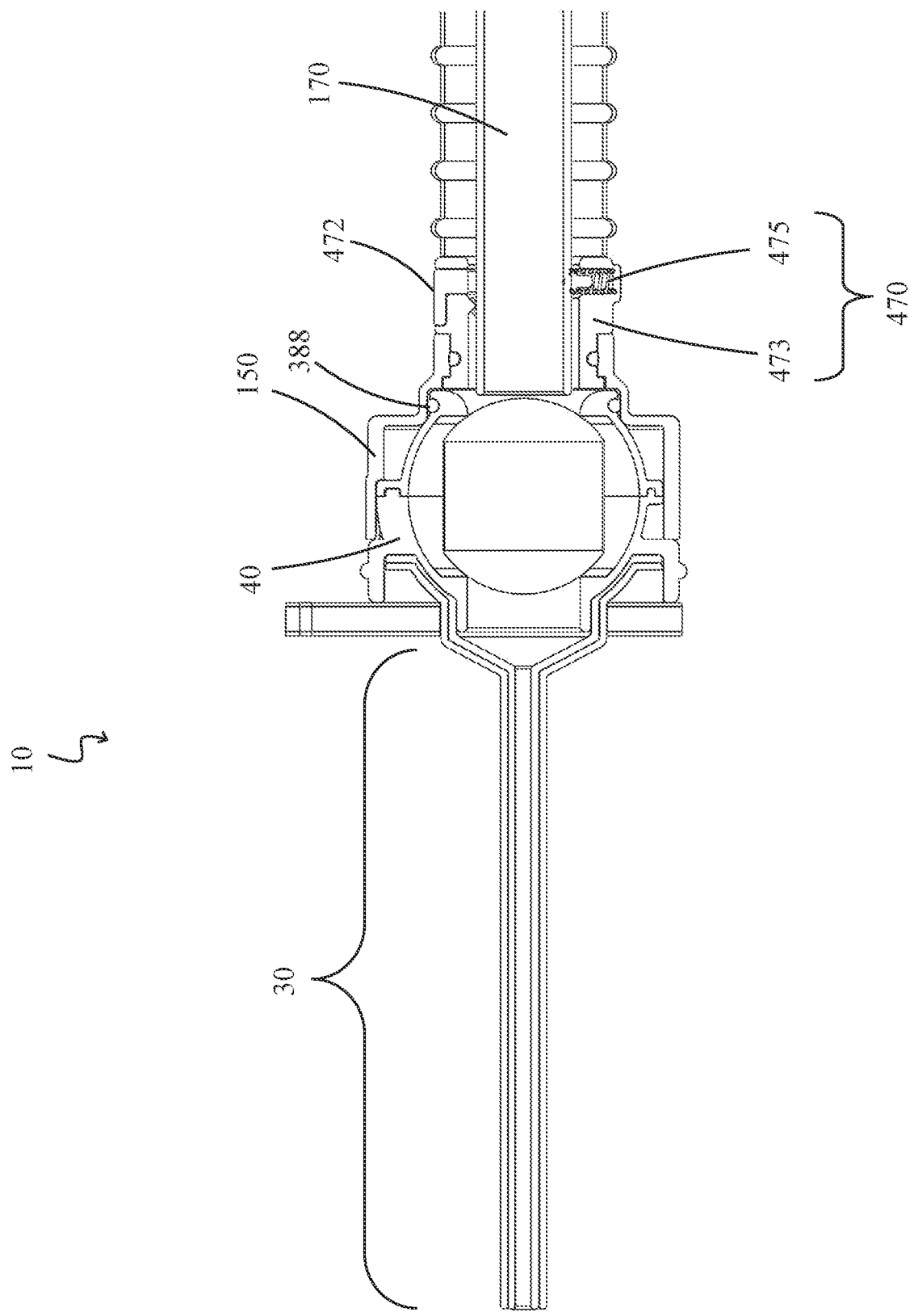
FIG. 10 is a cross-sectional view of access pathway connecting to the attachment device in accordance with an embodiment of the present invention.

FIGS. 9-10 depict the assembly upon reversible connection of attachment 140 to access pathway 20. The connection of access pathway port 40 to attachment connector 150 allows access pathway 20 and attachment 140 to securely connect and form an airtight seal via O-ring 388 (or, in other embodiments, via direct contact and/or a seat, washer, or related mechanism). Once connected, there is an uninterrupted transcutaneous access pathway from the body cavity through access pathway 20 to chest tube 170, through which chest tube 170 may be inserted into the body. Additionally shown is equipment locking mechanism 470 of attachment 140, including equipment lock 472, equipment lock holder 473, and spring 475. To move chest tube 170 forward or backwards in reference to attachment connector 150, the user must depress tube lock 472, thus displacing its internal ring so as to disconnect from and allow chest tube 170 to move. When no pressure is exerted on tube lock 472, spring 475 pushes tube lock 472 upwards to hold chest tube 170 in its desired position, once established.

Figure 11:
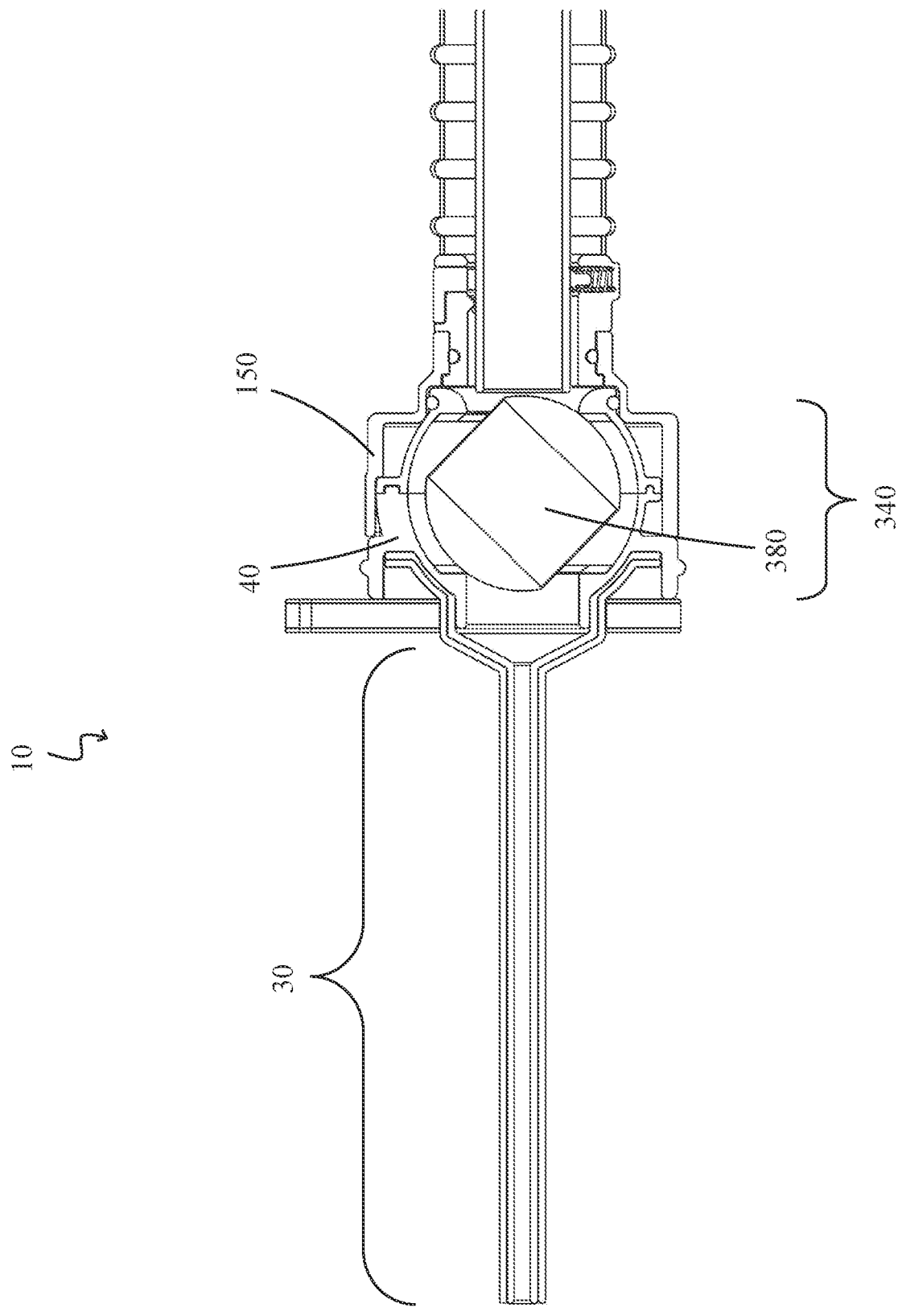
FIG. 11 is a cross-sectional side view of the device of FIG. 10, shown with the ball-valve mechanism partially engaged.
Figure 12:
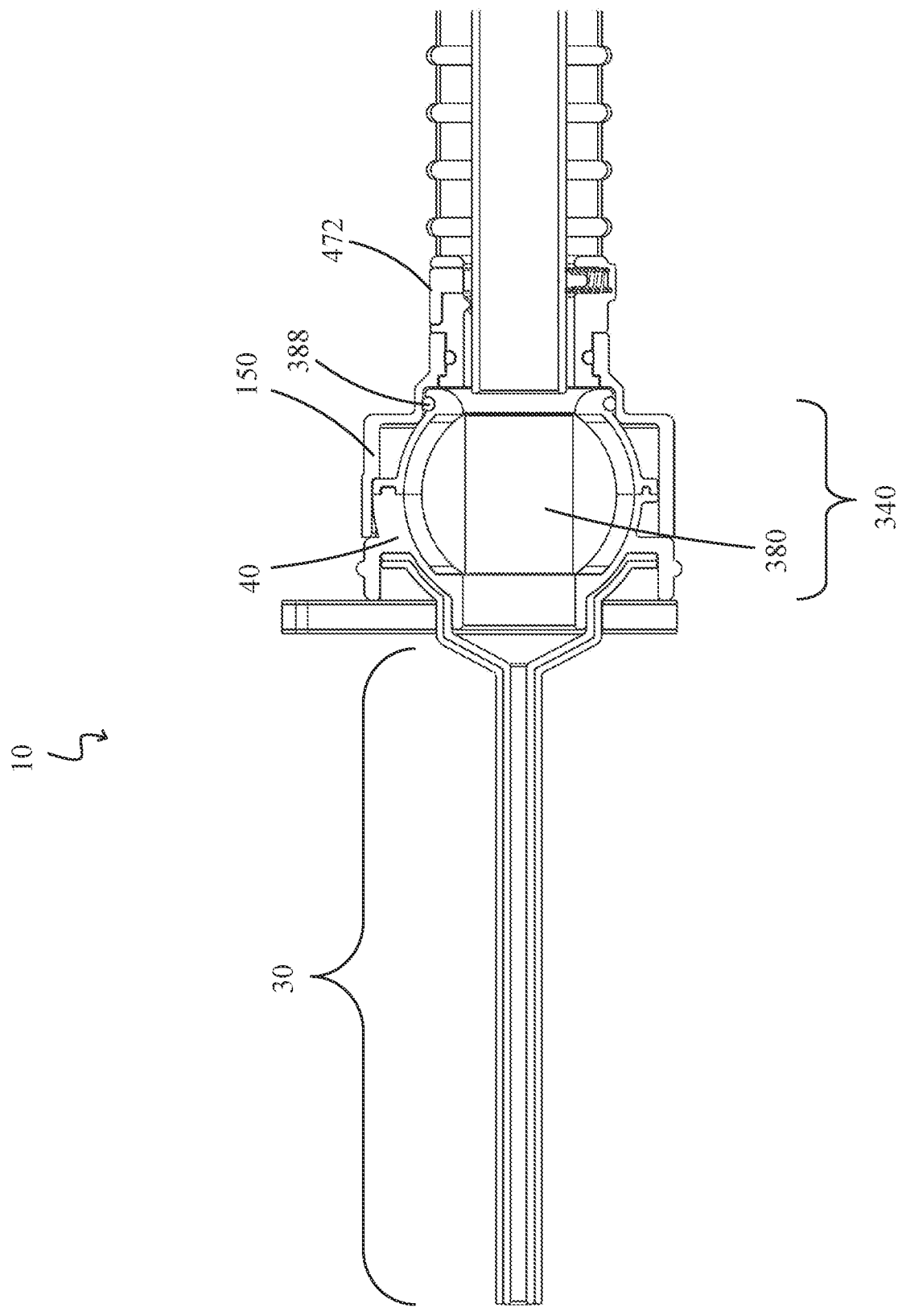
FIG. 12 is a cross-sectional side view of the device of FIG. 10, shown with the ball-valve mechanism fully engaged.
Figure 13:
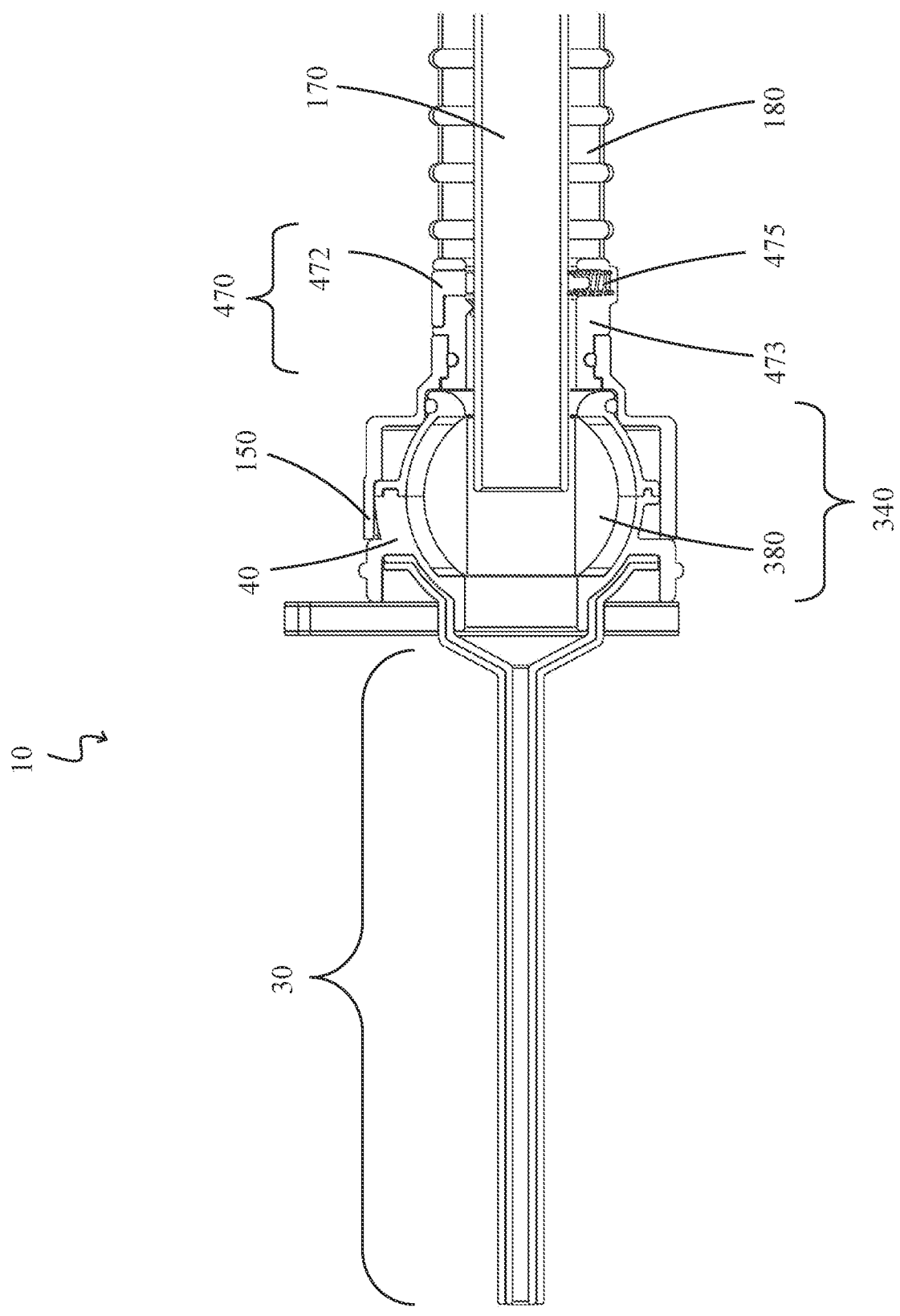
FIG. 13 is a cross-sectional side view of the device of FIG. 10, shown with the chest tube advancing distally.
Figure 14:
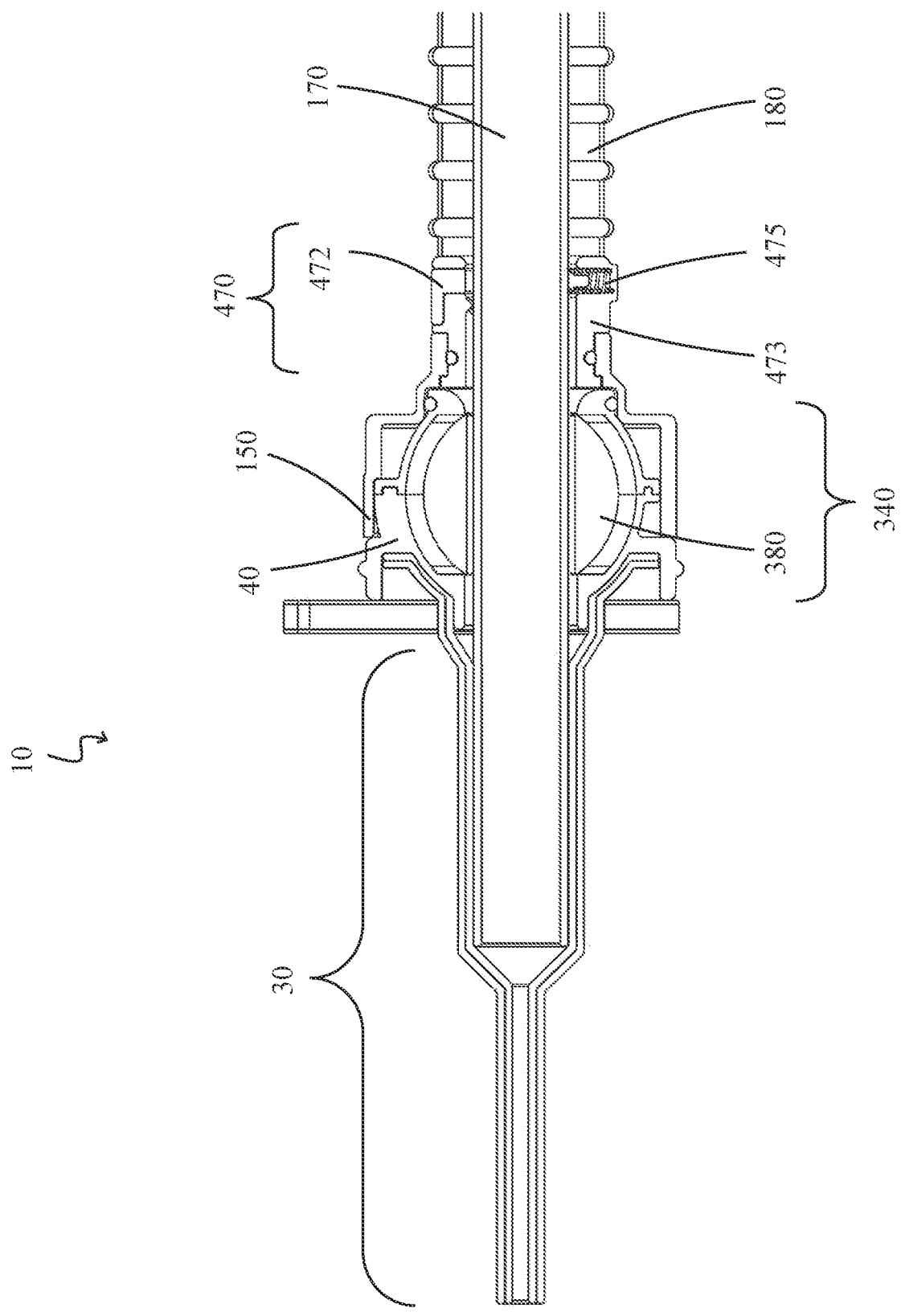
FIG. 14 is a cross-sectional side view of the device of FIG. 10, shown with the chest tube entering and dilating the catheter.
Figure 15:
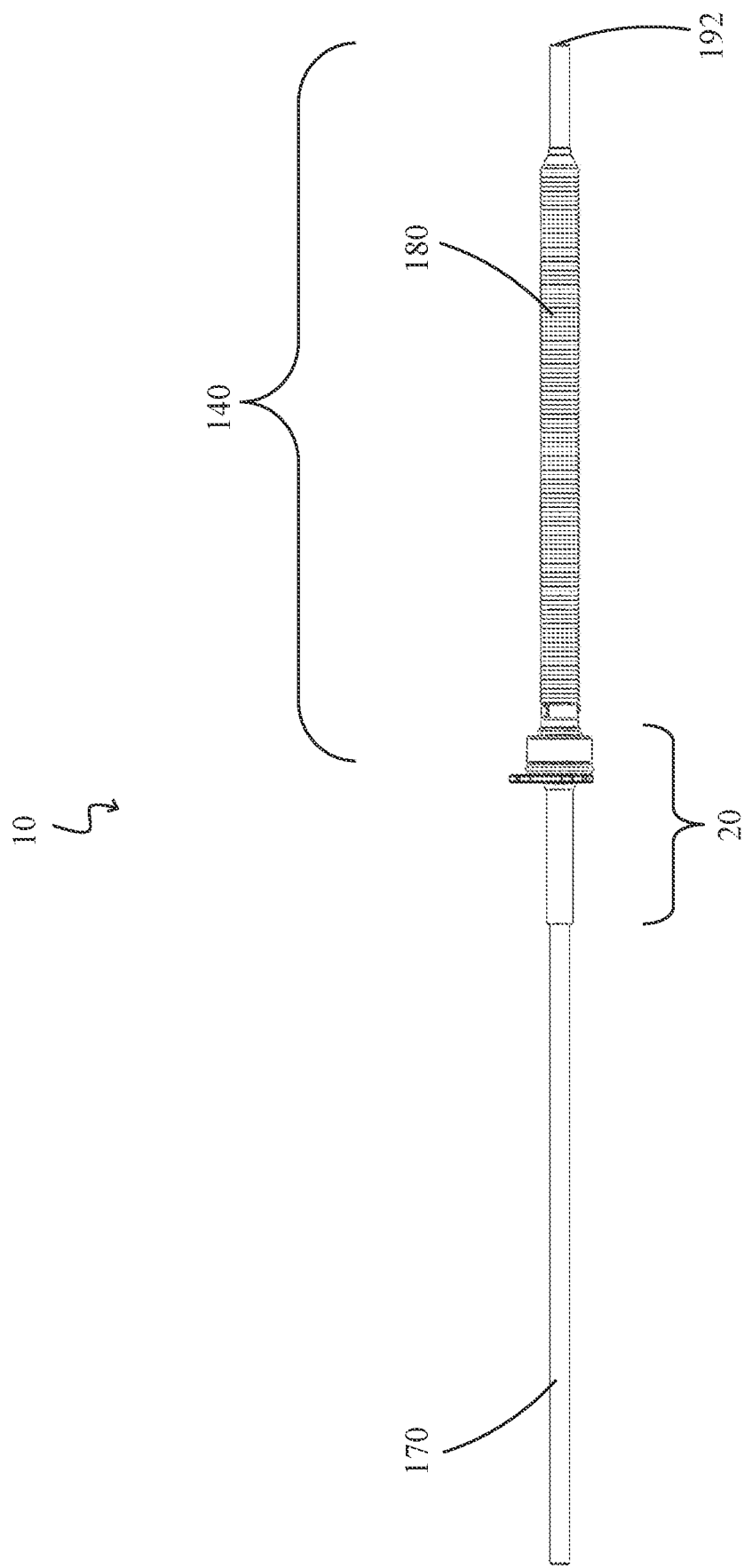
FIG. 15 is a side view of an attachment device, shown with a chest tube fully advanced through the access pathway, in accordance with an embodiment of the invention.
Figure 16:
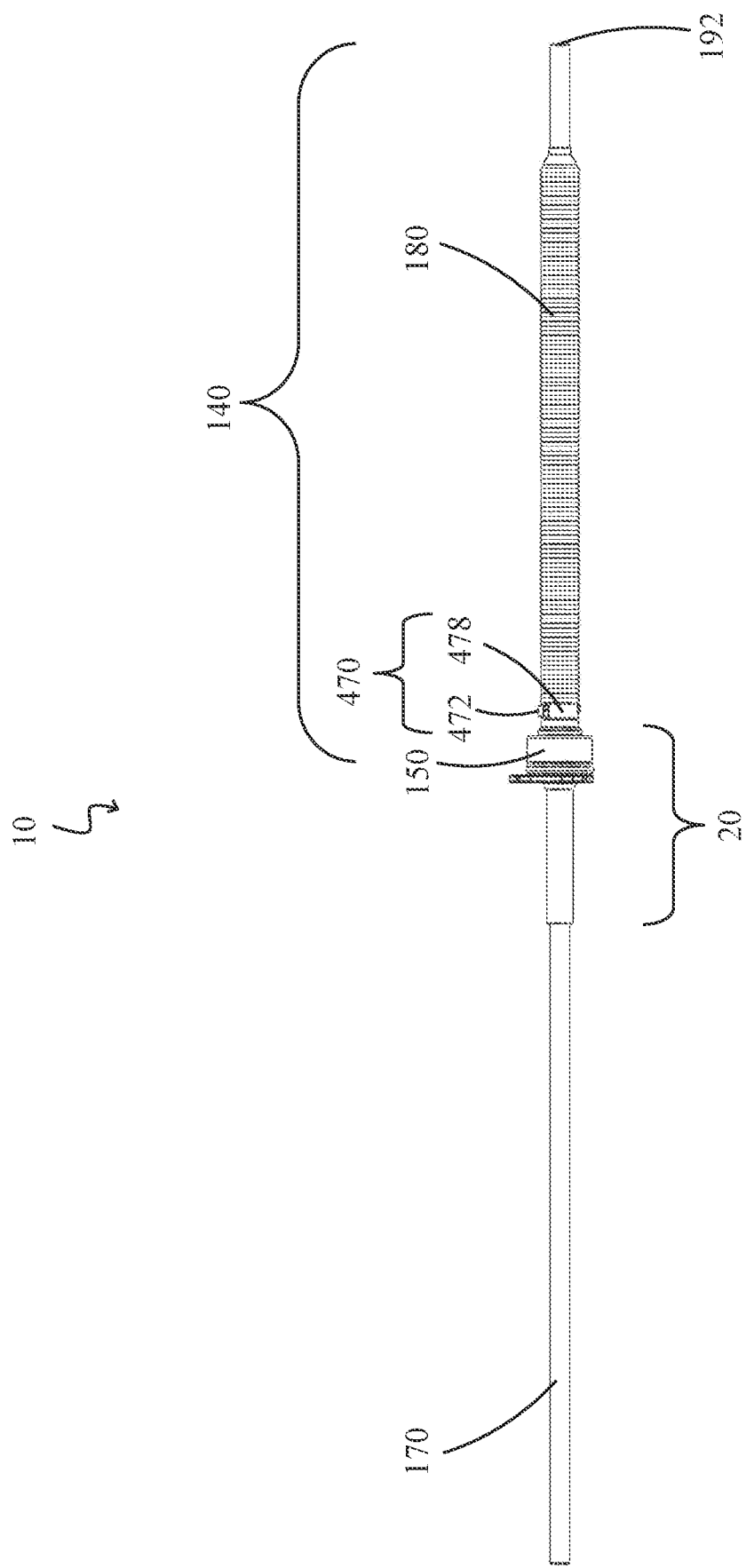
FIG. 16 is a side view of the device of FIG. 15, shown with the chest tube locking mechanism engaged.

Referring now to FIGS. 11-12, one benefit of embodiments of the device 10 is that it only allows access pathway port 40 to open when an opposing attachment connector 150 is attached and engaged. To open and engage, the user moves nob 462 and thus key 464 (see previous figures) on attachment connector 150, which in turn opens ball-valve mechanism 340. Key 464 moves trunnion feature 383 (see previous figures) on access pathway port 40 to turn port ball 380, which causes the ball-valve mechanism 340 to become in line with the inside of catheter 30, the proximal external surface of access pathway port 40, and attachment connector 150. As aforementioned, while engaged the device also prevents the removal of attachment connector 150 from access pathway port 40 via feature 386 and/or flange 375 (see previous figures).

Referring now to FIGS. 13-16, with port ball 380 in its open position, chest tube 170 may now advance through it into catheter 30 and the patient's chest cavity, as long as equipment locking mechanism 470 is disengaged. The opening of ball-valve mechanism 340 has created an uninterrupted transcutaneous access pathway within access pathway 20 and attachment connector 150. As such, when tube lock 472 is pressed down, chest tube 170 can be manipulated by the operator within collapsible sheath 180 to slide it distally through access pathway 20 and into the pleural space. One safety feature of the device is that attachment connector 150 is unable to be removed from access pathway 20 until chest tube 170 is pulled out and ball-valve mechanism 340 closed, ensuring that the external environment never communicates directly through an open ball-valve mechanism 340 to the body cavity (as long as the proximal end 192 of chest tube 170 is sealed). Once chest tube 170 is in the desired location, equipment locking mechanism 470 may be reversibly released (FIG. 16) to hold chest tube 170 at the desired length within the body. Because chest tube 170 is in the body, attachment connector 150 remains locked onto access pathway 20 until removal of chest tube 170 and closure of ball-valve mechanism 340.

Although not shown in the Figures, in some embodiments attachment 140 contains means to save the patient's blood for autotransfusion (discontinuous and/or continuous) and/or cell salvage. In various embodiments, this is provided by a feature that is connected onto chest tube suction apparatus (e.g. as is traditionally performed), directly onto the proximal end 192 of chest tube 170, and/or directly onto another attachment device embodiments (e.g. FIG. 18, FIG. 19). In some embodiments, this autotransfusion means is a bag, storage container, and/or other means for gathering and/or storing the patient's blood to allow autotransfusion back into the patient. In many of the embodiments, the autotransfusion means includes one or more filters (e.g. 200-micron filter) to facilitate autotransfusion. In various embodiments, autotransfusion means operates via gravity, pressure cuff, and/or continuous autotransfusion and/or additionally includes autotransfusion connector, reinfusion tubing, autotransfusion bag, and/or a method for measuring blood output.

Additionally, although not shown in the Figures, in some embodiments chest tube 170 has a check valve to prevent air and/or debris from entering the tube and body (e.g. Heimlich valve at its proximal end 192). Additionally, in some embodiments attachment 140 includes a device to produce vibration and/or agitation to chest tube 170 to better assist with suction and removal of material (e.g. retained hemothorax, pus). Additionally, in some embodiments, intrapleural thrombolytic agents, devices with one or more wires for chest tube de-clogging, and/or other prevention or treatment methods for retained hemothorax are used in conjunction with the device.

Additionally, although not shown in the Figures, in some embodiments the device includes an access port cap that can cover access pathway port 40 when it is closed and another attachment is not in use. This attachment securely covers access pathway port 40 without opening ball-valve mechanism 340, thus providing an additional barrier to entry of air, dust, dirt, and/or other external material. In some embodiments, this access port cap includes a modified nob 462 that locks the access port cap onto access pathway port 40 without opening ball-valve mechanism 340. In other embodiments, access port cap does not have nob 462 and/or has a locking mechanism on the other side (e.g. interacting with feature 386).

Figure 17:
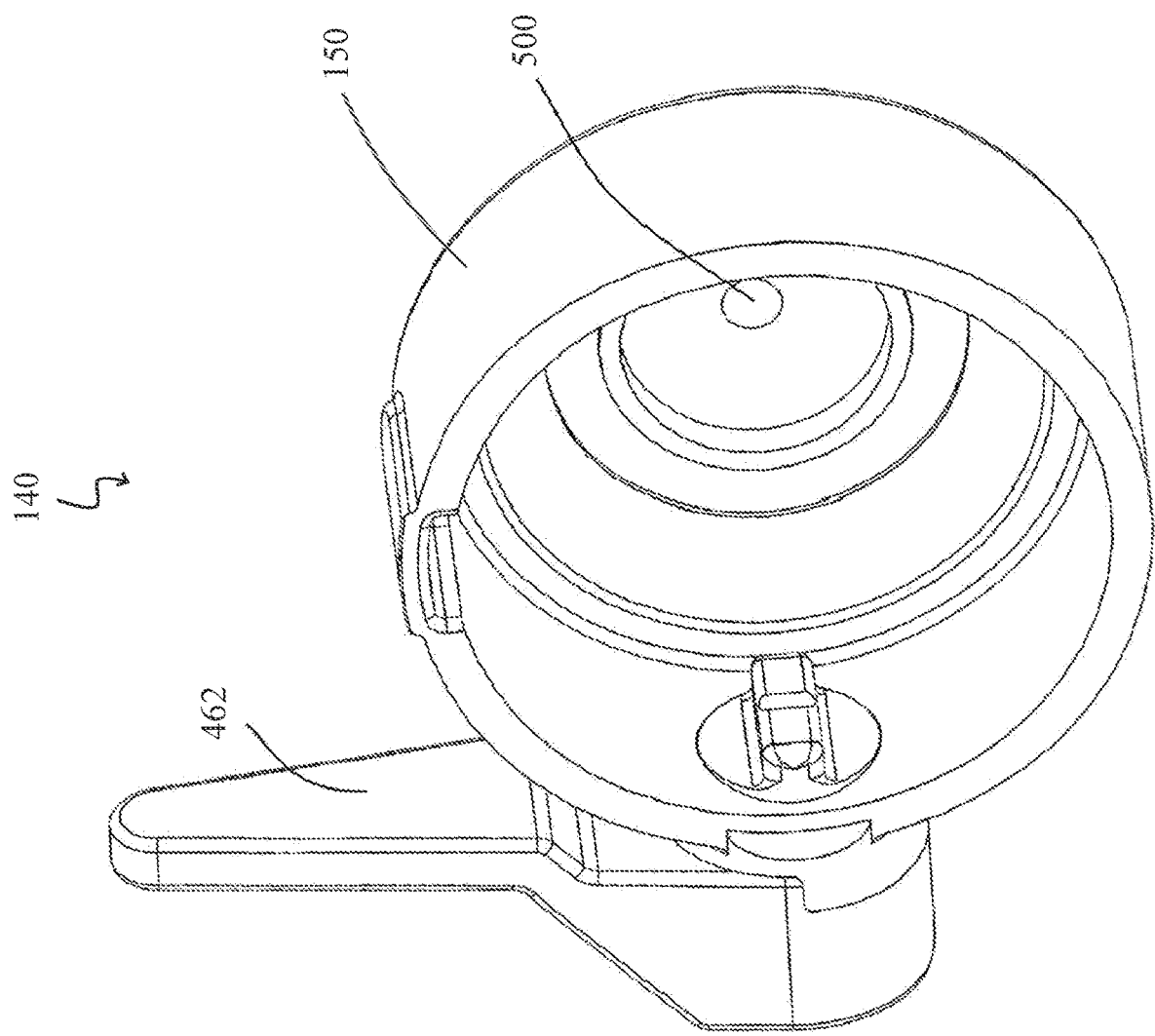
FIG. 17 depicts an attachment device containing a check valve in accordance with an embodiment of the invention.

Referring now to FIGS. 17-20, other embodiments of attachment 140 are shown. These embodiments can be used interchangeably with those described previously via reversible connection to access pathway port 40 and/or as part of system and/or kit that includes at least one port and one or more different attachment devices. FIG. 17 shows another embodiment of attachment 140. In this embodiment, connected to attachment connector 150 is one or more check valves 500. When connected to access pathway 20, this attachment allows air, fluid, and/or other debris to escape the body while preventing air, fluid, and/or other debris from entering access pathway 20. In various embodiments, this type of attachment is used in isolation (thus, not requiring external suction), connected to suction, and/or connected to an autotransfusion bag. Additionally, in various embodiments the check valve is one or more of a ball check valve, diaphragm check valve, stop-check valve, lift-check valve, in-line check valve, duckbill valve, Heimlich valve, and/or pneumatic non-return valve of various sizes. This embodiment contains no sheath or internal equipment component for insertion into the body. Nob 462 is shown in this embodiment as a lever.

Figure 18:
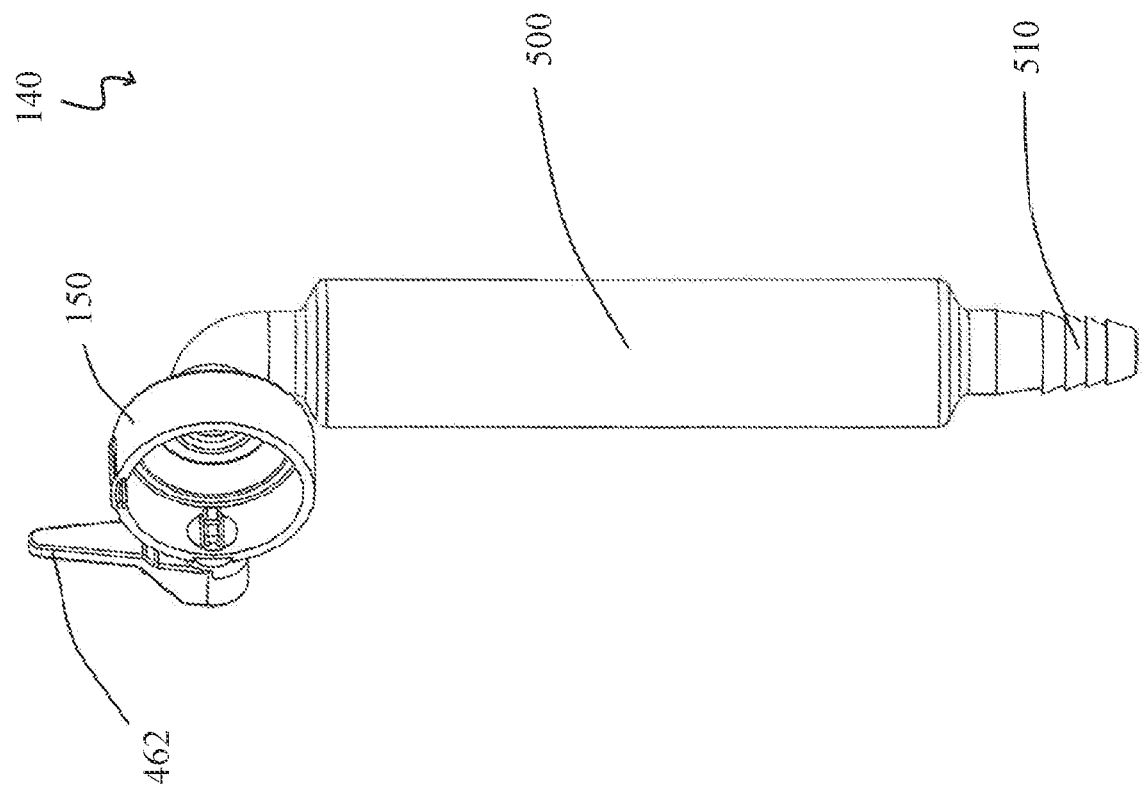
FIG. 18 depicts an attachment device containing a different type of check valve modified to facilitate attachment to suction and/or an autotransfusion means in accordance with an embodiment of the invention.

Referring now to FIG. 18, another embodiment of attachment 140 is shown. In this embodiment, connected to attachment connector 150 is a check valve 500 (e.g. a Heimlich valve) modified to facilitate attachment to suction and/or an autotransfusion means through proximal portion 510. This embodiment contains no sheath or internal equipment component for insertion into the body. Nob 462 is shown in this embodiment as a lever.

Figure 19:
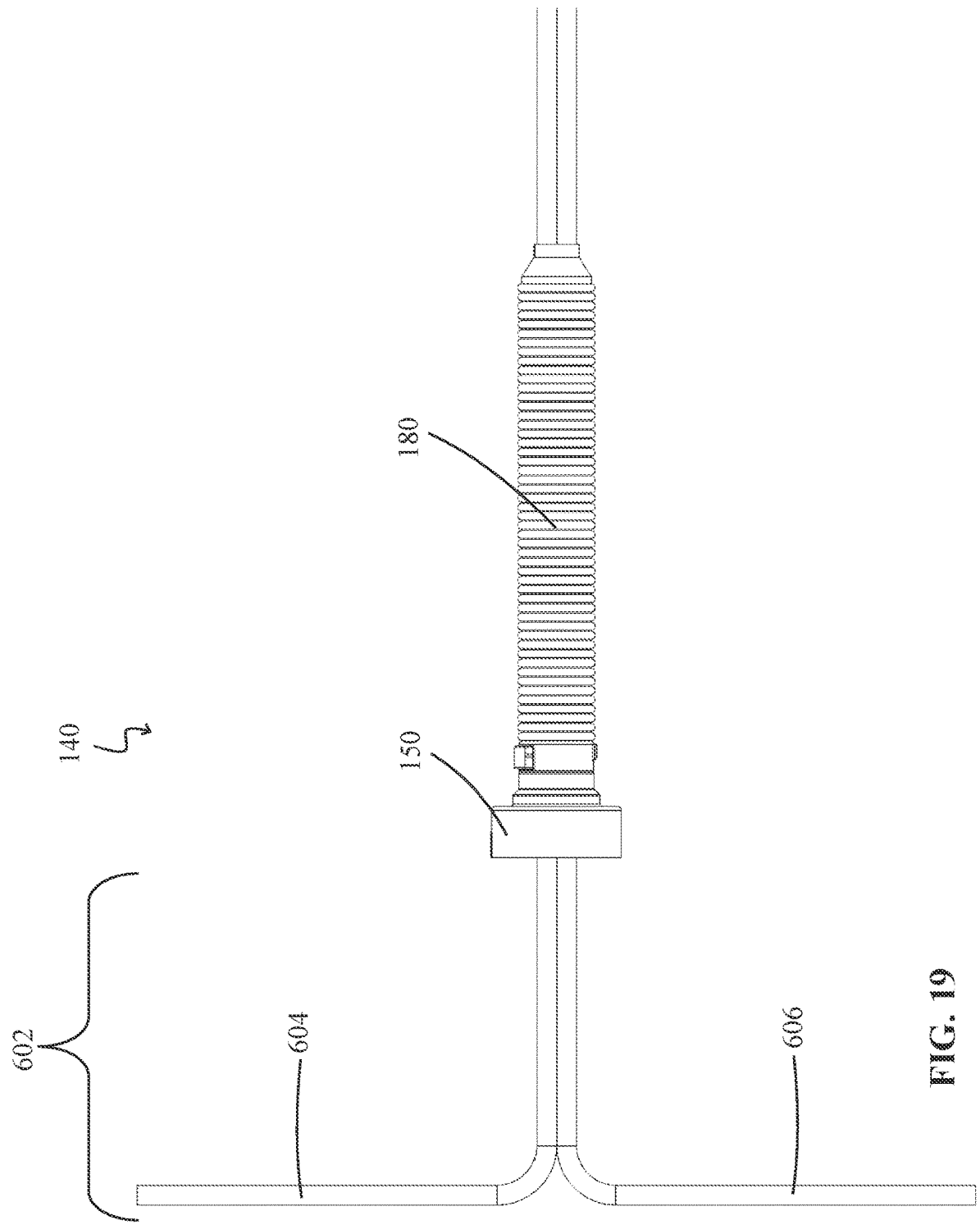
FIG. 19 depicts an attachment device containing an irrigation-suction system as an internal equipment component in accordance with an embodiment of the invention.

Referring now to FIG. 19, another embodiment of attachment 140 is shown. In this embodiment, the internal equipment component is a loop irrigation mechanism 602 at least partially sealed within the sheath 180 (shown with sheath 180 collapsed). The loop irrigation mechanism 602 includes irrigation tube 604 and drainage tube 606. This and related embodiments allow continuous and/or intermittent loop irrigation to prevent and/or treat retained hemothorax and/or other buildup within the body (e.g. the pleural cavity). This functions by having water, normal saline, and/or other solution enter the body through irrigation tube 604, wash through the body cavity, and then be removed by suction through drainage tube 606.

Figure 20:
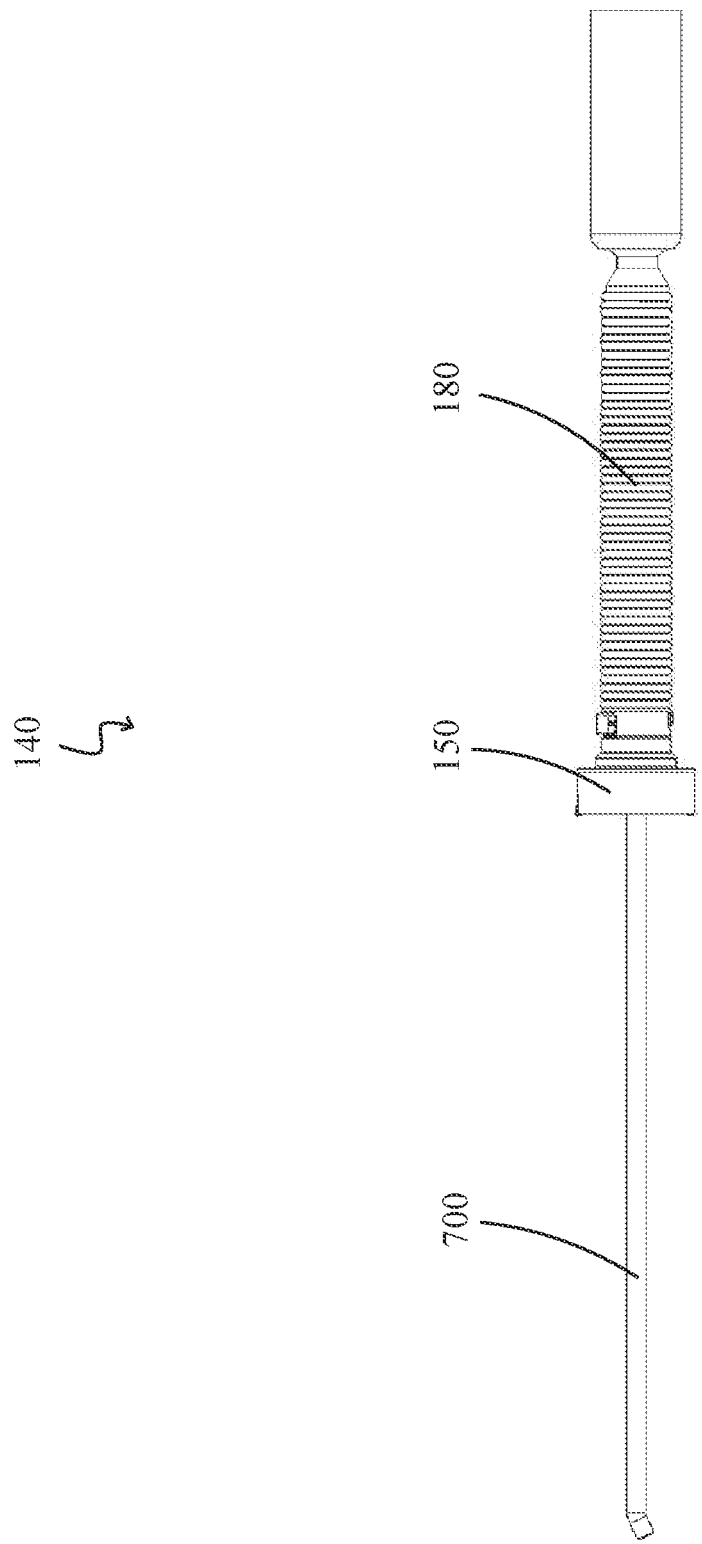
FIG. 20 depicts an attachment device containing an endoscopic camera as an internal equipment component in accordance with an embodiment of the invention.

Referring now to FIG. 20, another embodiment of attachment 140 is shown. In this embodiment, connected to attachment connector 150 is an endoscope 700 (e.g. a thoracoscope) at least partially sealed within sheath 180 (shown with sheath 180 collapsed). In this and related embodiments, a rigid and/or flexible endoscope tube (e.g. fiber-optic scope) is partially sealed within sheath 180 with the eyepiece and/or screen for image viewing located outside of the body. These embodiments include various sizes (e.g. 5-mm, 10-mm) and lenses (e.g. 0°, 30°) of endoscope. Some embodiments include an additional channel to also allow entry of medical instruments and/or manipulators. In this and related embodiments, the attachment can be used for thoracoscopy, pleuroscopy, other procedures involving the passage of an endoscope through the chest wall (e.g. fluid drainage, biopsy, pleurodesis), and/or other procedures involving the passage of an endoscope into the body.

Under various embodiments, these attachments facilitate the performance in a location without extensive sterility (e.g. out-of-hospital, on the battlefield, at the bedside, in the intensive care unit) of procedures currently performed in a sterile operating room (e.g. VATS). These procedures include but are not limited to evaluation of chest trauma, treatment of chest trauma, evaluation of diaphragmatic injury, treatment of diaphragmatic injury, lobectomy, wedge resection, decortication, tissue biopsy, stapled lung biopsy, pneumonectomy, resection of pulmonary nodule, evaluation of mediastinal tumors, evaluation of adenopathy, pleural biopsy, bullectomy, treatment of pneumothorax, management of empyema, pleurodesis of malignant effusions, repair of a bronchopleural fistula, pericardial window, sympathectomy, truncal vagotomy, pulmonary decortication, pleurodesis, lung biopsy, pleural biopsy, esophageal operation, mediastinal mass resection, and/or pulmonary lobectomy. Although multiple embodiments of attachment 140 are shown with different internal equipment components, the invention is not limited to the embodiments set forth herein for purposes of exemplification.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A device for forming and/or maintaining a percutaneous access pathway into a body of a patient, comprising:
an access pathway configured to allow access to an internal portion of a patient's body from an external environment, the access pathway comprising an access pathway port configured to maintain a non-pierceable barrier between the internal portion of the body and the external environment when in a closed position, wherein the access pathway port connects through a distal opening to an access pathway catheter extending at least partially into the internal portion of the body and allowing access into the internal portion of the body when the access pathway port is open; and
an attachment device connectable to the access pathway port and configured to open the access pathway port, the attachment device comprising an internally sterile attachment device sheath at least partially surrounding an internal equipment component of the attachment device, the attachment device sheath configured to enable insertion of at least part of the internal equipment component into the internal portion of the body through the access pathway when the attachment device is connected to the access pathway port.

2. The device of claim 1, wherein the internal equipment component of the attachment device is a chest tube.

3. The device of claim 1, wherein the attachment device includes a means for both irrigation and suction.

4. The device of claim 1, wherein the internal equipment component of the attachment device includes an endoscope.

5. The device of claim 1, wherein the internal equipment component of the attachment device includes one or more surgical tools.

6. The device of claim 1, wherein the attachment device sheath is configured to enable manipulation of the internal equipment component through the attachment device sheath while maintaining a barrier from the external environment to within the body.

7. The device of claim 6, wherein the attachment device sheath is air-impermeable.

8. The device of claim 1, wherein the access pathway port includes a mobile pathway or door that moves to open and close an entrance to the access pathway.

9. The device of claim 8, wherein the mobile pathway or door utilizes a cylinder, a sphere, a ball, or a ball-valve mechanism.

10. The device of claim 1, wherein the attachment device can be reversibly connected to and disconnected from the access pathway port.

11. The device of claim 1, wherein removal of the attachment device from the access pathway port is inhibited while the access pathway port is open.

12. The device of claim 1, wherein the attachment device is configured to connect to suction in the external environment.

13. The device of claim 1, wherein the access pathway contains a means for securing the access pathway to the body of a patient.

* * * * *